(12) United States Patent
Bernstein et al.

(10) Patent No.: US 11,264,133 B2
(45) Date of Patent: Mar. 1, 2022

(54) HEALTH MANAGEMENT DEVICES AND METHODS

(71) Applicant: Abbott Diabetes Care Inc., Alameda, CA (US)

(72) Inventors: Daniel Milfred Bernstein, El Granada, CA (US); Jared Watkin, Danville, CA (US); Martin J. Fennell, Concord, CA (US); Mark Kent Sloan, Redwood City, CA (US); Michael Love, Pleasanton, CA (US); Namvar Kiaie, Danville, CA (US); Jean-Pierre Cole, Tracy, CA (US); Steve Scott, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 17/157,611

(22) Filed: Jan. 25, 2021

(65) Prior Publication Data

US 2021/0151182 A1    May 20, 2021

Related U.S. Application Data

(63) Continuation of application No. 17/019,122, filed on Sep. 11, 2020, which is a continuation of application
(Continued)

(51) Int. Cl.
*A61B 5/145* (2006.01)
*G16H 10/00* (2018.01)
(Continued)

(52) U.S. Cl.
CPC ............ *G16H 40/67* (2018.01); *A61B 5/002* (2013.01); *A61B 5/0002* (2013.01);
(Continued)

(58) Field of Classification Search
None
See application file for complete search history.

(56) References Cited

U.S. PATENT DOCUMENTS 3,581,062 A    5/1971  Aston
3,926,760 A    12/1975 Allen et al.
(Continued)

FOREIGN PATENT DOCUMENTS

AU    2003/259741    2/2004
CA    2468577    6/2003
(Continued)

OTHER PUBLICATIONS

U.S. Appl. No. 17/019,122 (US 2021/0000396), filed Sep. 11, 2020 (Jan. 7, 2021).
(Continued)

*Primary Examiner* — Etsub D Berhanu
(74) *Attorney, Agent, or Firm* — Baker Botts L.L.P.

(57) ABSTRACT

Methods and devices and systems including a communication module operatively coupled to a data collection module for communicating the stored analyte related data after the analyte related data is stored in the data collection module over a predetermined time period, and a user interface unit configured to communicate with the communication module to receive from the communication module the stored analyte related data in the data collection module over the predetermined time period, and to output information associated with the monitored analyte level, where the user interface unit is configured to operate in a prospective analysis mode including substantially real time output of information associated with the monitored analyte level, or a retrospective analysis mode including limited output of information during the predetermined time period wherein
(Continued)

no information related to the monitored analyte level is output during the predetermined time period, are provided.

23 Claims, 9 Drawing Sheets

Related U.S. Application Data

No. 16/032,017, filed on Jul. 10, 2018, which is a continuation of application No. 14/094,719, filed on Dec. 2, 2013, now abandoned, which is a continuation of application No. 12/143,731, filed on Jun. 20, 2008, now Pat. No. 8,597,188.

(60) Provisional application No. 60/945,579, filed on Jun. 21, 2007.

(51) Int. Cl.
*G16H 40/67* (2018.01)
*A61B 5/1486* (2006.01)
*A61B 5/00* (2006.01)
*G16H 40/63* (2018.01)
*G16H 50/20* (2018.01)
*H04L 67/12* (2022.01)
*G06Q 50/22* (2018.01)
*G16H 10/60* (2018.01)
*G16Z 99/00* (2019.01)
*G08C 17/02* (2006.01)
*G16H 10/40* (2018.01)
*G16H 20/10* (2018.01)

(52) U.S. Cl.
CPC ...... *A61B 5/14532* (2013.01); *A61B 5/14542* (2013.01); *A61B 5/14546* (2013.01); *A61B 5/14865* (2013.01); *G06Q 50/22* (2013.01); *G08C 17/02* (2013.01); *G16H 10/40* (2018.01); *G16H 10/60* (2018.01); *G16H 40/63* (2018.01); *G16H 50/20* (2018.01); *G16Z 99/00* (2019.02); *H04L 67/12* (2013.01); *A61B 5/0017* (2013.01); *A61B 5/0031* (2013.01); *A61B 2560/0223* (2013.01); *A61B 2560/0252* (2013.01); *A61B 2560/0276* (2013.01); *A61B 2560/045* (2013.01); *A61B 2560/0456* (2013.01); *G16H 20/10* (2018.01)

(56) References Cited

U.S. PATENT DOCUMENTS

| | | |
|---|---|---|
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,684,245 A | 8/1987 | Goldring |
| 4,703,324 A | 10/1987 | White |
| 4,703,756 A | 11/1987 | Gough et al. |
| 4,711,245 A | 12/1987 | Higgins et al. |
| 4,731,726 A | 3/1988 | Allen, II |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,818,994 A | 4/1989 | Orth et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,124,661 A | 6/1992 | Zellin et al. |
| 5,135,004 A | 8/1992 | Adams et al. |
| 5,165,407 A | 11/1992 | Wilson et al. |
| 5,245,314 A | 9/1993 | Kah et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,289,497 A | 2/1994 | Jackobson et al. |
| 5,293,877 A | 3/1994 | O'Hara et al. |
| 5,299,571 A | 4/1994 | Mastrototaro |
| 5,305,008 A | 4/1994 | Turner et al. |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,340,722 A | 8/1994 | Wolfbeis et al. |
| 5,342,408 A | 8/1994 | deCoriolis et al. |
| 5,342,789 A | 8/1994 | Chick et al. |
| 5,356,786 A | 10/1994 | Heller et al. |
| 5,360,404 A | 11/1994 | Novacek et al. |
| 5,372,133 A | 12/1994 | Hogen Esch |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,400,794 A | 3/1995 | Gorman |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,051 A | 10/1995 | Oka et al. |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,543,326 A | 8/1996 | Heller et al. |
| 5,544,196 A | 8/1996 | Tiedmann, Jr. et al. |
| 5,558,638 A | 9/1996 | Evers et al. |
| 5,568,806 A | 10/1996 | Cheney, II et al. |
| 5,569,186 A | 10/1996 | Lord et al. |
| 5,581,206 A | 12/1996 | Chevallier et al. |
| 5,582,184 A | 12/1996 | Erickson et al. |

(56) References Cited

U.S. PATENT DOCUMENTS

| | | |
|---|---|---|
| 5,586,553 A | 12/1996 | Halili et al. |
| 5,593,852 A | 1/1997 | Heller et al. |
| 5,600,301 A | 2/1997 | Robinson, III |
| 5,601,435 A | 2/1997 | Quy |
| 5,609,575 A | 3/1997 | Larson et al. |
| 5,623,933 A | 4/1997 | Amano et al. |
| 5,628,310 A | 5/1997 | Rao et al. |
| 5,628,890 A | 5/1997 | Carter et al. |
| 5,634,468 A | 6/1997 | Platt et al. |
| 5,653,239 A | 8/1997 | Pompei et al. |
| 5,659,454 A | 8/1997 | Vermesse |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,733,259 A | 3/1998 | Valcke et al. |
| 5,733,313 A | 3/1998 | Barreras., Sr. et al. |
| 5,735,285 A | 4/1998 | Albert et al. |
| 5,748,103 A | 5/1998 | Flach et al. |
| 5,749,907 A | 5/1998 | Mann |
| 5,758,290 A | 5/1998 | Neal et al. |
| 5,772,586 A | 6/1998 | Heinonen et al. |
| 5,778,879 A | 7/1998 | Ota et al. |
| 5,791,344 A | 8/1998 | Schulman et al. |
| 5,798,961 A | 8/1998 | Hey et al. |
| 5,804,047 A | 9/1998 | Karube et al. |
| 5,820,551 A | 10/1998 | Hill et al. |
| 5,822,715 A | 10/1998 | Worthington et al. |
| 5,830,064 A | 11/1998 | Bradish et al. |
| 5,833,603 A | 11/1998 | Kovacs et al. |
| 5,856,758 A | 1/1999 | Joffe et al. |
| 5,891,049 A | 4/1999 | Cyrus et al. |
| 5,899,855 A | 5/1999 | Brown |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,071,391 A | 6/2000 | Gotoh et al. |
| 6,083,710 A | 7/2000 | Heller et al. |
| 6,085,342 A | 7/2000 | Marholev et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,097,480 A | 8/2000 | Kaplan |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,198,946 B1 | 3/2001 | Shin et al. |
| 6,200,265 B1 | 3/2001 | Walsh et al. |
| 6,203,495 B1 | 3/2001 | Bardy et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,478,736 B1 | 11/2002 | Mault |
| 6,484,045 B1 | 11/2002 | Holker et al. |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,503,381 B1 | 1/2003 | Gotoh et al. |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |

(56) References Cited

U.S. PATENT DOCUMENTS

| | | |
|---|---|---|
| 6,605,201 B1 | 8/2003 | Mao et al. |
| 6,607,509 B2 | 8/2003 | Bobroff et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,668,196 B1 | 12/2003 | Villegas et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,748,445 B1 | 6/2004 | Darcey et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,973,706 B2 | 12/2005 | Say et al. |
| 6,974,437 B2 | 12/2005 | Lebel et al. |
| 6,983,867 B1 | 1/2006 | Fugere |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,020,508 B2 | 3/2006 | Stivoric et al. |
| 7,022,072 B2 | 4/2006 | Fox et al. |
| 7,024,236 B2 | 4/2006 | Ford et al. |
| 7,024,245 B2 | 4/2006 | Lebel et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,124,027 B1 | 10/2006 | Ernst et al. |
| 7,125,382 B2 | 10/2006 | Zhou et al. |
| 7,134,999 B2 | 11/2006 | Brauker et al. |
| 7,136,689 B2 | 11/2006 | Shults et al. |
| 7,154,398 B2 | 12/2006 | Chen et al. |
| 7,155,290 B2 | 12/2006 | Von Arx et al. |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,276,146 B2 | 10/2007 | Wilsey |
| 7,276,147 B2 | 10/2007 | Wilsey |
| 7,278,983 B2 | 10/2007 | Ireland et al. |
| 7,286,894 B1 | 10/2007 | Grant et al. |
| 7,287,318 B2 | 10/2007 | Bhullar et al. |
| 7,291,497 B2 | 11/2007 | Holmes et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr/Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,386,937 B2 | 6/2008 | Bhullar et al. |
| 7,387,010 B2 | 6/2008 | Sunshine et al. |
| 7,399,277 B2 | 7/2008 | Saidara et al. |
| 7,401,111 B1 | 7/2008 | Batman et al. |
| 7,402,153 B2 | 7/2008 | Steil et al. |
| 7,404,796 B2 | 7/2008 | Ginsberg |
| 7,408,132 B2 | 8/2008 | Wambsganss et al. |
| 7,419,573 B2 | 9/2008 | Gundel |

(56) References Cited

U.S. PATENT DOCUMENTS

| | | |
|---|---|---|
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbies et al. |
| 7,651,596 B2 | 1/2010 | Petisce et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,741,734 B2 | 6/2010 | Joannopoulos et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,813,809 B2 | 10/2010 | Strother et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,955,258 B2 | 6/2011 | Goscha et al. |
| 7,970,448 B2 | 6/2011 | Shults et al. |
| 7,974,672 B2 | 7/2011 | Shults et al. |
| 7,976,467 B2 | 7/2011 | Young et al. |
| 7,978,063 B2 | 7/2011 | Baldus et al. |
| 7,999,674 B2 | 8/2011 | Kamen |
| 8,000,918 B2 | 8/2011 | Fjield et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,538,512 B1 | 9/2013 | Bibian et al. |
| 8,617,069 B2 | 12/2013 | Bernstein et al. |
| 8,808,515 B2 | 8/2014 | Feldman et al. |
| 9,736,210 B2 | 8/2017 | Root et al. |
| 2001/0016682 A1 | 8/2001 | Berner et al. |
| 2001/0037060 A1 | 11/2001 | Thompson et al. |
| 2001/0037366 A1 | 11/2001 | Webb et al. |
| 2001/0047127 A1 | 11/2001 | New et al. |
| 2002/0013522 A1 | 1/2002 | Lay et al. |
| 2002/0013538 A1 | 1/2002 | Teller |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019606 A1 | 2/2002 | Lebel et al. |
| 2002/0023852 A1 | 2/2002 | McIvor et al. |
| 2002/0039026 A1 | 4/2002 | Stroth et al. |
| 2002/0042090 A1 | 4/2002 | Heller et al. |
| 2002/0045808 A1 | 4/2002 | Ford et al. |
| 2002/0049482 A1 | 4/2002 | Fabian et al. |
| 2002/0050250 A1 | 5/2002 | Peterson et al. |
| 2002/0065454 A1 | 5/2002 | Lebel et al. |
| 2002/0072784 A1 | 6/2002 | Sheppard et al. |
| 2002/0074162 A1 | 6/2002 | Su et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0103499 A1 | 8/2002 | Perez et al. |
| 2002/0106709 A1 | 8/2002 | Potts et al. |
| 2002/0118528 A1 | 8/2002 | Su et al. |
| 2002/0128594 A1 | 9/2002 | Das et al. |
| 2002/0161288 A1 | 10/2002 | Shin et al. |
| 2002/0164836 A1 | 11/2002 | Ho |
| 2002/0169635 A1 | 11/2002 | Shillingburg |
| 2002/0183604 A1 | 12/2002 | Gowda et al. |
| 2002/0185128 A1 | 12/2002 | Theobald |
| 2002/0185130 A1 | 12/2002 | Wright et al. |
| 2002/0197522 A1 | 12/2002 | Lawrence et al. |
| 2003/0004403 A1 | 1/2003 | Drinan et al. |
| 2003/0020477 A1 | 1/2003 | Goldstein |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0065308 A1 | 4/2003 | Lebel et al. |
| 2003/0076792 A1 | 4/2003 | Theimer |
| 2003/0078481 A1 | 4/2003 | McIvor et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0114898 A1 | 6/2003 | Von Arx et al. |
| 2003/0119457 A1 | 6/2003 | Standke |

(56) References Cited

U.S. PATENT DOCUMENTS

| | | |
|---|---|---|
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0144579 A1 | 7/2003 | Buss |
| 2003/0144581 A1 | 7/2003 | Conn et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0188427 A1 | 10/2003 | Say et al. |
| 2003/0199790 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey/Willuhn et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0063435 A1 | 4/2004 | Sakamoto et al. |
| 2004/0064068 A1 | 4/2004 | DeNuzzio et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikiey et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204635 A1* | 10/2004 | Scharf ............... G16H 40/63 600/323 |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0221057 A1 | 11/2004 | Darcey et al. |
| 2004/0223876 A1 | 11/2004 | Kirollos et al. |
| 2004/0225199 A1 | 11/2004 | Evanyk et al. |
| 2004/0225338 A1 | 11/2004 | Lebel et al. |
| 2004/0236200 A1 | 11/2004 | Say et al. |
| 2004/0240426 A1 | 12/2004 | Wu et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0103624 A1 | 5/2005 | Bhullar et al. |
| 2005/0104457 A1 | 5/2005 | Jordan et al. |
| 2005/0112169 A1 | 5/2005 | Brauker et al. |
| 2005/0112544 A1 | 5/2005 | Xu et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0171442 A1 | 8/2005 | Shirasaki et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0215871 A1 | 9/2005 | Feldman et al. |
| 2005/0221504 A1 | 10/2005 | Petruno et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0277164 A1 | 12/2005 | Drucker et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0004272 A1 | 1/2006 | Shah et al. |
| 2006/0009727 A1 | 1/2006 | O'Mahony et al. |
| 2006/0010098 A1 | 1/2006 | Goodnow et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |

(56) References Cited

U.S. PATENT DOCUMENTS

| | | |
|---|---|---|
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040793 A1 | 2/2006 | Martens et al. |
| 2006/0042080 A1 | 3/2006 | Say et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0091006 A1 | 5/2006 | Wang et al. |
| 2006/0129733 A1 | 6/2006 | Solbelman |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbies et al. |
| 2006/0183985 A1 | 8/2006 | Brister et al. |
| 2006/0189863 A1 | 8/2006 | Peyser et al. |
| 2006/0193375 A1 | 8/2006 | Lee et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0220839 A1 | 10/2006 | Fifolt et al. |
| 2006/0222566 A1 | 10/2006 | Brauker et al. |
| 2006/0224059 A1* | 10/2006 | Swedlow ........... A61B 5/14551 600/323 |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0272652 A1 | 12/2006 | Stocker et al. |
| 2006/0276714 A1 | 12/2006 | Holt et al. |
| 2006/0287586 A1* | 12/2006 | Murphy ................. G16H 40/67 600/300 |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0090511 A1 | 4/2007 | Borland et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0111196 A1 | 5/2007 | Alarcon et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoy et al. |
| 2007/0179352 A1 | 8/2007 | Randlov et al. |
| 2007/0191701 A1 | 8/2007 | Feldman et al. |
| 2007/0197889 A1 | 8/2007 | Brister et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255125 A1 | 11/2007 | Moberg et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285299 A1 | 12/2007 | Batra |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt/Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0033268 A1 | 2/2008 | Stafford et al. |
| 2008/0039702 A1 | 2/2008 | Hayter et al. |
| 2008/0045824 A1 | 2/2008 | Tapsak et al. |
| 2008/0055070 A1 | 3/2008 | Bange et al. |
| 2008/0058625 A1 | 3/2008 | McGarraugh et al. |
| 2008/0059227 A1 | 3/2008 | Clapp |
| 2008/0060955 A1 | 3/2008 | Goodnow |
| 2008/0062055 A1 | 3/2008 | Cunningham et al. |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0097908 A1 | 4/2008 | Dicks et al. |
| 2008/0102441 A1 | 5/2008 | Chen et al. |
| 2008/0108942 A1 | 5/2008 | Brister et al. |
| 2008/0119705 A1 | 5/2008 | Patel et al. |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |

(56) References Cited

U.S. PATENT DOCUMENTS

| | | |
|---|---|---|
| 2008/0179187 A1 | 7/2008 | Ouyang |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Car/Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1* | 12/2008 | Rankers ............ G16H 15/00 604/504 |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054748 A1 | 2/2009 | Feldman et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0076356 A1 | 3/2009 | Simpson et al. |
| 2009/0076359 A1 | 3/2009 | Peyser et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0085873 A1 | 4/2009 | Betts et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch/Menges et al. |
| 2009/0216100 A1 | 8/2009 | Ebner et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard/Sorensen |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |

(56) References Cited

U.S. PATENT DOCUMENTS

| | | |
|---|---|---|
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0113897 A1 | 5/2010 | Brenneman et al. |
| 2010/0119693 A1 | 5/2010 | Tapsak et al. |
| 2010/0119881 A1 | 5/2010 | Patel et al. |
| 2010/0121169 A1 | 5/2010 | Petisce et al. |
| 2010/0152548 A1 | 6/2010 | Koski |
| 2010/0152554 A1 | 6/2010 | Steine et al. |
| 2010/0160757 A1 | 6/2010 | Weinert et al. |
| 2010/0160759 A1 | 6/2010 | Celentano et al. |
| 2010/0168538 A1 | 7/2010 | Keenan et al. |
| 2010/0190435 A1 | 7/2010 | Cook et al. |
| 2010/0191087 A1 | 7/2010 | Talbot et al. |
| 2010/0198142 A1 | 8/2010 | Sloan et al. |
| 2010/0213080 A1 | 8/2010 | Celentano et al. |
| 2010/0228111 A1 | 9/2010 | Friman et al. |
| 2010/0230285 A1 | 9/2010 | Hoss et al. |
| 2010/0235439 A1 | 9/2010 | Goodnow et al. |
| 2010/0259543 A1 | 10/2010 | Tarassenko et al. |
| 2010/0267161 A1 | 10/2010 | Wu et al. |
| 2010/0312176 A1 | 12/2010 | Lauer et al. |
| 2010/0313105 A1 | 12/2010 | Nekoomaram et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331651 A1 | 12/2010 | Groll |
| 2011/0004085 A1 | 1/2011 | Mensinger et al. |
| 2011/0004276 A1 | 1/2011 | Blair et al. |
| 2011/0021889 A1 | 1/2011 | Hoss et al. |
| 2011/0022411 A1 | 1/2011 | Hjelm et al. |
| 2011/0077469 A1 | 3/2011 | Blocker et al. |
| 2011/0097090 A1 | 4/2011 | Cao |
| 2011/0123971 A1 | 5/2011 | Berkowitz et al. |
| 2011/0125040 A1 | 5/2011 | Crawford et al. |
| 2011/0137571 A1 | 6/2011 | Power et al. |
| 2011/0148905 A1 | 6/2011 | Simmons et al. |
| 2011/0152637 A1 | 6/2011 | Kateraas et al. |
| 2011/0184482 A1 | 7/2011 | Eberman et al. |
| 2011/0184752 A1 | 7/2011 | Ray et al. |
| 2011/0208027 A1 | 8/2011 | Wagner et al. |
| 2011/0213225 A1 | 9/2011 | Bernstein et al. |
| 2011/0230741 A1 | 9/2011 | Liang et al. |
| 2011/0257895 A1 | 10/2011 | Brauker et al. |
| 2011/0263959 A1 | 10/2011 | Young et al. |
| 2011/0264378 A1 | 10/2011 | Breton et al. |
| 2011/0287528 A1 | 11/2011 | Fern et al. |
| 2011/0288574 A1 | 11/2011 | Curry et al. |
| 2011/0319729 A1 | 12/2011 | Donnay et al. |
| 2012/0010642 A1 | 1/2012 | Lee et al. |
| 2013/0111248 A1 | 5/2013 | Ghesquiere et al. |
| 2015/0326072 A1 | 11/2015 | Petras et al. |

FOREIGN PATENT DOCUMENTS

| | | |
|---|---|---|
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2617965 | 10/2011 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 0680727 | 11/1995 |
| EP | 0724859 | 8/1996 |
| EP | 0805574 | 11/1997 |
| EP | 0973289 | 1/2000 |
| EP | 0678308 | 5/2000 |
| EP | 1048264 | 11/2000 |
| EP | 1292218 | 3/2003 |
| EP | 1077634 | 7/2003 |
| EP | 1568309 | 8/2005 |
| EP | 1666091 | 6/2006 |
| EP | 1703697 | 9/2006 |
| EP | 1704893 | 9/2006 |
| EP | 1956371 | 8/2008 |
| EP | 2031534 | 3/2009 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| EP | 1725163 | 12/2010 |
| EP | 2260757 | 12/2010 |
| EP | 2201969 | 3/2011 |
| EP | 1413245 | 6/2011 |
| EP | 2153382 | 2/2012 |
| EP | 2284773 | 2/2012 |
| GB | 2409951 | 7/2005 |
| JP | 07/311196 | 11/1995 |
| JP | 10/305016 | 11/1998 |
| JP | 11/056823 | 3/1999 |
| JP | 2000/060803 | 2/2000 |
| JP | 2000/354591 | 12/2000 |
| JP | 2001/353159 | 12/2001 |
| JP | 2002/513602 | 5/2002 |
| JP | 2003/108677 | 4/2003 |
| JP | 2003/144417 | 5/2003 |
| JP | 2003/215122 | 7/2003 |
| JP | 2003/520091 | 7/2003 |
| JP | 2004/147705 | 5/2004 |
| JP | 2005/218492 | 8/2005 |
| JP | 2006/021031 | 1/2006 |

(56) References Cited

FOREIGN PATENT DOCUMENTS

| | | |
|---|---|---|
| JP | 2006/048404 | 2/2006 |
| JP | 2006/055530 | 3/2006 |
| JP | 2006/280464 | 10/2006 |
| JP | 2006/288619 | 10/2006 |
| JP | 2006/289081 | 10/2006 |
| JP | 2007/144141 | 6/2007 |
| JP | 2007/152037 | 6/2007 |
| WO | WO 1995/028878 | 2/1995 |
| WO | WO 1996/025089 | 8/1996 |
| WO | WO/1996/035370 | 11/1996 |
| WO | WO 1997/033513 | 9/1997 |
| WO | WO 1998/004902 | 2/1998 |
| WO | WO 1998/035053 | 8/1998 |
| WO | WO 1999/27849 | 6/1999 |
| WO | WO 1999/28736 | 6/1999 |
| WO | WO 1999/056613 | 11/1999 |
| WO | WO 2000/049940 | 8/2000 |
| WO | WO 2000/059370 | 10/2000 |
| WO | WO 2000/060350 | 10/2000 |
| WO | WO 2000/074753 | 12/2000 |
| WO | WO 2000/078992 | 12/2000 |
| WO | WO 2001/052935 | 7/2001 |
| WO | WO 2001/054753 | 8/2001 |
| WO | WO 2002/016905 | 2/2002 |
| WO | WO 2002/058537 | 8/2002 |
| WO | WO 2003/057027 | 7/2003 |
| WO | WO 2003/076893 | 9/2003 |
| WO | WO 2003/082091 | 10/2003 |
| WO | WO 2003/085372 | 10/2003 |
| WO | WO 2004/015539 | 2/2004 |
| WO | WO 2004/047445 | 6/2004 |
| WO | WO 2004/061420 | 7/2004 |
| WO | WO 2004/090503 | 10/2004 |
| WO | WO 2004/098405 | 11/2004 |
| WO | WO 2005/041766 | 5/2005 |
| WO | WO 2005/045744 | 5/2005 |
| WO | WO 2005/057175 | 6/2005 |
| WO | WO 2005/065538 | 7/2005 |
| WO | WO 2005/089103 | 9/2005 |
| WO | WO 2005/121785 | 12/2005 |
| WO | WO 2006/017358 | 2/2006 |
| WO | WO 2006/020212 | 2/2006 |
| WO | WO 2006/024671 | 3/2006 |
| WO | WO 2006/026741 | 3/2006 |
| WO | WO 2006/032653 | 3/2006 |
| WO | WO 2006/064397 | 6/2006 |
| WO | WO 2006/072035 | 7/2006 |
| WO | WO 2006/079114 | 7/2006 |
| WO | WO 2006/086423 | 8/2006 |
| WO | WO 2006/118947 | 11/2006 |
| WO | WO 2006/124099 | 11/2006 |
| WO | WO 2007/007459 | 1/2007 |
| WO | WO 2007/016399 | 2/2007 |
| WO | WO 2007/019289 | 2/2007 |
| WO | WO 2007/027788 | 3/2007 |
| WO | WO 2007/041069 | 4/2007 |
| WO | WO 2007/041070 | 4/2007 |
| WO | WO 2007/041248 | 4/2007 |
| WO | WO 2007/056638 | 5/2007 |
| WO | WO 2007/065285 | 6/2007 |
| WO | WO 2007/101223 | 9/2007 |
| WO | WO 2007/120363 | 10/2007 |
| WO | WO 2007/126444 | 11/2007 |
| WO | WO 2007/053832 | 12/2007 |
| WO | WO 2007/143225 | 12/2007 |
| WO | WO 2007/149319 | 12/2007 |
| WO | WO 2008/001366 | 1/2008 |
| WO | WO 2008/021913 | 2/2008 |
| WO | WO 2008/042760 | 4/2008 |
| WO | WO 2008/048452 | 4/2008 |
| WO | WO 2008/052374 | 5/2008 |
| WO | WO 2008/062099 | 5/2008 |
| WO | WO 2008/086541 | 7/2008 |
| WO | WO 2008/115409 | 9/2008 |
| WO | WO 2008/128210 | 10/2008 |
| WO | WO 2008/130896 | 10/2008 |
| WO | WO 2008/130897 | 10/2008 |
| WO | WO 2008/130898 | 10/2008 |
| WO | WO 2008/143943 | 11/2008 |
| WO | WO 2008/144445 | 11/2008 |
| WO | WO 2008/153693 | 12/2008 |
| WO | WO 2009/018058 | 2/2009 |
| WO | WO 2009/086216 | 7/2009 |
| WO | WO 2009/096992 | 8/2009 |
| WO | WO 2009/097594 | 8/2009 |
| WO | WO 2010/062898 | 6/2010 |
| WO | WO 2010/077329 | 7/2010 |
| WO | WO 2011/000528 | 1/2011 |
| WO | WO 2011/022418 | 2/2011 |
| WO | WO/011/104616 | 9/2011 |

OTHER PUBLICATIONS

U.S. Appl. No. 16/032,017 (US 2018/0325434), filed Jul. 10, 2018 (Nov. 15, 2018).
U.S. Appl. No. 14/094,719 (US 2014/0088382), filed Dec. 2, 2013 (Mar. 27, 2014).
U.S. Appl. No. 12/143,731 (US 2008/0319295), filed Jun. 20, 2008 (Dec. 25, 2008).
U.S. Appl. No. 17/019,122, Jan. 21, 2021 Non-Final Office Action.
U.S. Appl. No. 17/019,122, Dec. 18, 2020 Response to Restriction Requirement.
U.S. Appl. No. 17/019,122, Dec. 15, 2020 Restriction Requirement.
U.S. Appl. No. 16/032,017, Jan. 6, 2021 Non-Final Office Action.
U.S. Appl. No. 14/094,719, Feb. 6, 2020 Abandonment.
U.S. Appl. No. 14/094,719, Jul. 10, 2019 Final Office Action.
U.S. Appl. No. 14/094,719, Mar. 14, 2019 Response After Non-Final Office Action.
U.S. Appl. No. 14/094,719, Dec. 26, 2018 Non-Final Office Action.
U.S. Appl. No. 14/094,719, Nov. 28, 2018 Request for Continued Examination.
U.S. Appl. No. 14/094,719, Nov. 28, 2018 Response After Final Office Action.
U.S. Appl. No. 14/094,719, Aug. 28, 2018 Final Office Action.
U.S. Appl. No. 14/094,719, Jul. 24, 2018 Supplemental Response.
U.S. Appl. No. 14/094,719, Apr. 21, 2018 Response After Non-Final Office Action.
U.S. Appl. No. 14/094,719, Jan. 25, 2018 Non-Final Office Action.
U.S. Appl. No. 14/094,719, Sep. 27, 2017 Request for Continued Examination.
U.S. Appl. No. 14/094,719, Sep. 27, 2017 Response After Final Office Action.
U.S. Appl. No. 14/094,719, Mar. 31, 2017 Final Office Action.
U.S. Appl. No. 14/094,719, Dec. 28, 2016 Response After Non-Final Office Action.
U.S. Appl. No. 14/094,719, Sep. 28, 2016 Non-Final Office Action.
U.S. Appl. No. 14/094,719, Oct. 2, 2015 Preliminary Amendment.
U.S. Appl. No. 12/143,731, Oct. 31, 2013 Issue Fee Payment.
U.S. Appl. No. 12/143,731, Sep. 27, 2013 Notice of Allowance.
U.S. Appl. No. 12/143,731, Sep. 11, 2013 Response After Final Office Action.
U.S. Appl. No. 12/143,731, Jul. 17, 2013 Final Office Action.
U.S. Appl. No. 12/143,731, Jul. 12, 2013 Response After Non-Final Office Action.
U.S. Appl. No. 12/143,731, Oct. 18, 2012 Non-Final Office Action.
U.S. Appl. No. 12/143,731, Jul. 19, 2012 Response After Non-Final Office Action.
U.S. Appl. No. 12/143,731, Jul. 19, 2012 Non-Final Office Action.
U.S. Appl. No. 12/143,731, Jan. 17, 2012 Response After Non-Final Office Action.
U.S. Appl. No. 12/143,731, Oct. 17, 2011 Non-Final Office Action.
Armour, J. C., et al., "Application of Chronic Intravascular Blood Glucose Sensor in Dogs", Diabetes, vol. 39, 1990, pp. 1519/1526.
Australian Patent Application No. 2008265541, Examiner's Report dated Nov. 29, 2013.
Australian Patent Application No. 2008265541, Examiner's Report dated Oct. 15, 2012.

(56) References Cited

OTHER PUBLICATIONS

Australian Patent Application No. 2008265542, Examiner's Report dated Oct. 4, 2012.
Australian Patent Application No. 2013205279, Examiner's Report dated Aug. 8, 2014.
Australian Patent Application No. 2015275271, Examiner's Report dated Feb. 13, 2017.
Australian Patent Application No. 2017254903, Examiner's Report dated Dec. 11, 2018.
Australian Patent Application No. 2018200899, Examiner's Report dated Dec. 6, 2018.
Bennion, N., et al., "Alternate Site Glucose Testing: A Crossover Design", Diabetes Technology & Therapeutics, vol. 4, No. 1, 2002, pp. 25/33.
Blank, T. B., et al., "Clinical Results From a Non/Invasive Blood Glucose Monitor", Optical Diagnostics and Sensing of Biological Fluids and Glucose and Cholesterol Monitoring II, Proceedings of SPIE, vol. 4624, 2002, pp. 1/10.
Brooks, S. L., et al., "Development of an on/Line Glucose Sensor for Fermentation Monitoring", Biosensors, vol. 3, 1987/88, pp. 45/56.
Canadian Patent Application No. 2,690,870, Examiner's Report dated Feb. 24, 2015.
Canadian Patent Application No. 2,690,742, Examiner's Report mailed Dec. 30, 2015.
Canadian Patent Application No. 2,690,870, Examiner's Report mailed Mar. 23, 2016.
Canadian Patent Application No. 2,690,742, Examiner's Report mailed Oct. 24, 2016.
Canadian Patent Application No. 2,690,742. Notice of Allowance dated Sep. 26, 2017.
Cass, A. E., et al., "Ferrocene/Medicated Enzyme Electrode for Amperometric Determination of Glucose", Analytical Chemistry, vol. 56 No. 4, 1984, 667/671.
Chinese Patent Application No. 200880021299.1, English Translation & Original Language of Office Action dated Aug. 15, 2011.
Chinese Patent Application No. 200880021299.1, English Translation & Original Language of Office Action dated Dec. 14, 2010.
Chinese Patent Application No. 200880021299.1, English Translation & Original Language of Office Action dated May 22, 2012.
Chinese Patent Application No. 201310161229.9, Original Language & English Translation of Office Action dated Jun. 3, 2014.
Chinese Patent Application No. 201310161229.9, Original Language & English Translation of Office Action dated Feb. 17, 2015.
Chinese Patent Application No. 201310161229.9, Original Language & English Translation of Office Action dated Jul. 30, 2015.
Chinese Patent Application No. 201310161229.9, Original Language & English Translation of Office Action dated Feb. 23, 2016.
Csoregi, E., et al., "Design and Optimization of a Selective Sub-cutaneously Implantable Glucose Electrode Based on 'Wired' Glucose Oxidase", Analytical Chemistry, vol. 67, No. 7, 1995, pp. 1240/1244.
Diem, P., et al., "Clinical Performance of a Continuous Viscometric Affinity Sensor for Glucose", Diabetes Technology & Therapeutics, vol. 6, 2004, pp. 790/799.
El/Khatib, F. H, et al., "Adaptive Closed/Loop Control Provides Blood/Glucose Regulation Using Subcutaneous Insulin and Glucagon Infusion in Diabetic Swine", Journal of Diabetes, Science and Technology, vol. 1, No. 2, 2007, pp. 181/192.
European Patent Application No. 08745799.0, Extended European Search Report dated Oct. 16, 2012.
European Patent Application No. 08771681.7, Extended European Search Report dated Oct. 16, 2012.
European Patent Application No. 08771682.5, Extended European Search Report dated May 11, 2012.
European Patent Application No. 08771681.7, Examination Report dated Jun. 6, 2014.
European Patent Application No. 08771682.5, Examination Report dated Dec. 18, 2015.
European Patent Application No. 08771681.7, Examination Report dated Jun. 17, 2016.
European Patent Application No. 08771682.5, Examination Report dated Jun. 29, 2016.
European Patent Application No. 08771682.5, Examination Report dated Feb. 2, 2017.
European Patent Application No. 08771681.7, Examination Report dated May 10, 2017.
European Patent Application No. 08771682.5, Examination Report dated Aug. 2, 2017.
European Patent Application No. 10739031.2, Opposition filed Dec. 20, 2018.
European Patent Application No. 13000105.0, Opposition filed Jan. 4, 2019.
European Patent Application No. 18192278.2, Extended European Search Report dated Mar. 13, 2019.
Feldman, B., et al., "A Continuous Glucose Sensor Based on Wired Enzyme™ Technology /Results from a 3/Day Trial in Patients with Type 1 Diabetes", Diabetes Technology & Therapeutics, vol. 5, No. 5, 2003, pp. 769/779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Garg, S., et al., "Improvement in Glycemic Excursions with a Transcutaneous, Real/Time Continuous Glucose Sensor", Diabetes Care, vol. 29, No. 1, 2006, pp. 44/50.
Hao, Y., "Topical Review; Wireless Body Sensor Networks for Health/Monitoring Applications", Physiological Measurement, vol. 29, No. 11, Nov. 1, 2008, pp. R27/R56.
Indian Patent Application No. 8050/DELNP/2009, Examination Report dated Jun. 19, 2017.
Isermann, R., "Supervision, Fault/Detection and Fault/Diagnosis Methods / An Introduction", Control Engineering Practice, vol. 5, No. 5, 1997, pp. 639/652.
Isermann, R., et al., "Trends in the Application of Model/Based Fault Detection and Diagnosis of Technical Processes", Control Engineering Practice, vol. 5, No. 5, 1997, pp. 709/719.
Japanese Patent Application No. 2010/513476, English Translation of Office Action dated Jul. 23, 2013.
Japanese Patent Application No. 2010/513477, Original Language & English Translation of Office Action dated May 13, 2014.
Japanese Patent Application No. 2010/513476, Original Language and English Translation of Office Action dated Jun. 24, 2014.
Japanese Patent Application No. 2014/187515, Original Language & English Translation of Office Action dated Aug. 18, 2015.
Japanese Patent Application No. 2014/187515, Original Language & English Translation of Office Action dated Jul. 5, 2016.
Japanese Patent Application No. 2016/217028, Original Language & English Translation of Office Action dated Sep. 5, 2017.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303/1304.
Kaplan, S. M., "Wiley Electrical and Electronics Engineering Dictionary", IEEE Press, 2004, pp. 141, 142, 548, 549.
Kondepati, V., et al., "Recent Progress in Analytical Instrumentation for Glycemic Control in Diabetic and Critically Ill Patients", Analytical Bioanalytical Chemistry, vol. 388, 2007, pp. 545/ 563.
Lo, B., et al., "Key Technical Challenges and Current Implementations of Body Sensor Networks", Body Sensor Networks, 2005, pp. 1/5.
Lodwig, V., et al., "Continuous Glucose Monitoring with Glucose Sensors: Calibration and Assessment Criteria", Diabetes Technology & Therapeutics, vol. 5, No. 4, 2003, pp. 573/587.
Lortz, J., et al., "What is Bluetooth? We Explain the Newest Short/Range Connectivity Technology", Smart Computing Learning Series, Wireless Computing, vol. 8, Issue 5, 2002, pp. 72/74.

(56) References Cited

OTHER PUBLICATIONS

Malin, S. F., et al., "Noninvasive Prediction of Glucose by Near/Infrared Diffuse Reflectance Spectoscopy", Clinical Chemistry, vol. 45, No. 9, 1999, pp. 1651/1658.
McGarraugh, G., et al., "Glucose Measurements Using Blood Extracted from the Forearm and the Finger", TheraSense, Inc., 2001, 16 Pages.
McGarraugh, G., et al., "Physiological Influences on Off/Finger Glucose Testing", Diabetes Technology & Therapeutics, vol. 3, No. 3, 2001, pp. 367/376.
McKean, B. D., et al., "A Telemetry/Instrumentation System for Chronically Implanted Glucose and Oxygen Sensors", IEEE Transactions on Biomedical Engineering, vol. 35, No. 7, 1988, pp. 526/532.
PCT Application No. PCT/US2008/067792, International Preliminary Report on Patentability dated Jan. 7, 2010.
PCT Application No. PCT/US2008/067792, International Search Report and Written Opinion of the International Searching Authority dated Sep. 30, 2008.
PCT Application No. PCT/US2008/067793, International Preliminary Report on Patentability dated Jan. 7, 2010.
PCT Application No. PCT/US2008/067793, International Search Report and Written Opinion of the International Searching Authority dated Sep. 8, 2008.
Pickup, J., et al., "Implantable Glucose Sensors: Choosing the Appropriate Sensing Strategy", Biosensors, vol. 3, 1987/88, pp. 335/346.
Pickup, J., et al., "In Vivo Molecular Sensing in Diabetes Mellitus: An Implantable Glucose Sensor with Direct Electron Transfer", Diabetologia, vol. 32, 1989, pp. 213/217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268/2272.
Quinn, C. P., et al., "Kinetics of Glucose Delivery to Subcutaneous Tissue in Rats Measured with 0.3/mm Amperometric Microsensors", The American Physiological Society, 1995, E155/ E161.
Rodriguez, N., et al., "Flexible Communication and Control Protocol for Injectable Neuromuscular Interfaces", IEEE Transactions on Biomedical Circuits and Systems, IEEE, vol. 1 No. 1, 2007, pp. 19/27.
Roe, J. N., et al., "Bloodless Glucose Measurements", Critical Review in Therapeutic Drug Carrier Systems, vol. 15, Issue 3, 1998, pp. 199/241.
Sakakida, M., et al., "Development of Ferrocene/Mediated Needle/Type Glucose Sensor as a Measure of True Subcutaneous Tissue Glucose Concentrations", Artificial Organs Today, vol. 2, No. 2, 1992, pp. 145/158.
Sakakida, M., et al., "Ferrocene/Mediated Needle/Type Glucose Sensor Covered with Newly Designed Biocompatible Membrane", Sensors and Actuators B, vol. 13/14, 1993, pp. 319/322.
Salditt, P., "Trends in Medical Device Design and Manufacturing", SMTA News and Journal of Surface Mount Technology, vol. 17, 2004, pp. 19/24.
Salehi, C., et al., "A Telemetry/Instrumentation System for Long/Term Implantable Glucose and Oxygen Sensors", Analytical Letters, vol. 29, No. 13, 1996, pp. 2289/2308.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294/299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401/406.
Shichiri, M., et al., "Glycaemic Control in Pancreatectomized Dogs with a Wearable Artificial Endocrine Pancreas", Diabetologia, vol. 24, 1983, pp. 179/184.
Shichiri, M., et al., "In Vivo Characteristics of Needle/Type Glucose Sensor / Measurements of Subcutaneous Glucose Concentrations in Human Volunteers", Hormone and Metabolic Research Supplement Series, vol. 20, 1988, pp. 17/20.
Shichiri, M., et al., "Membrane Design for Extending the Long/Life of an Implantable Glucose Sensor", Diabetes Nutrition and Metabolism, vol. 2, 1989, pp. 309/313.
Shichiri, M., et al., "Needle/type Glucose Sensor for Wearable Artificial Endocrine Pancreas", Implantable Sensors for Closed/Loop Prosthetic Systems, Chapter 15, 1985, pp. 197/210.
Shichiri, M., et al., "Telemetry Glucose Monitoring Device With Needle/Type Glucose Sensor: A Useful Tool for Blood Glucose Monitoring in Diabetic Individuals", Diabetes Care, vol. 9, No. 3, 1986, pp. 298/301.
Shichiri, M., et al., "Wearable Artificial Endocrine Pancreas With Needle/Type Glucose Sensor", The Lancet, 1982, pp. 1129/1131.
Shults, M. C., et al., "A Telemetry/Instrumentation System for Monitoring Multiple Subcutaneously Implanted Glucose Sensors", IEEE Transactions on Biomedical Engineering, vol. 41, No. 10, 1994, pp. 937/942.
Sternberg, R., et al., "Study and Development of Multilayer Needle/Type Enzyme/Based Glucose Microsensors", Biosensors, vol. 4, 1988, pp. 27/40.
Thompson, M., et al., "In Vivo Probes: Problems and Perspectives", Clinical Biochemistry, vol. 19, 1986, pp. 255/261.
Tung, S., "Layers of Security for Active RFID Tags", RFID Handbook: Applications, Technology, Security, and Privacy, Edited by Ehson, et al., Chapter 33, 2008, pp. 1/28.
Turner, A., et al., "Diabetes Mellitus: Biosensors for Research and Management", Biosensors, vol. 1, 1985, pp. 85/115.
Updike, S. J., et al., "Principles of Long/Term Fully Implanted Sensors with Emphasis on Radiotelemetric Monitoring of Blood Glucose from Inside a Subcutaneous Foreign Body Capsule (FBC)", Biosensors in the Bod : Continuous in vivo Monitoring, Chapter 4, 1997, pp. 117/137.
U.S. Appl. No. 12/143,734, Advisory Action dated Oct. 11, 2012.
U.S. Appl. No. 12/143,734, Office Action dated Jan. 23, 2013.
U.S. Appl. No. 12/143,734, Office Action dated Jan. 27, 2012.
U.S. Appl. No. 12/143,734, Office Action dated Jul. 25, 2012.
U.S. Appl. No. 12/143,734, Office Action dated Oct. 14, 2011.
U.S. Appl. No. 12/625,510, Office Action dated Mar. 15, 2013.
U.S. Appl. No. 12/625,510, Office Action dated May 23, 2012.
U.S. Appl. No. 12/625,510, Office Action dated Aug. 20, 2012.
U.S. Appl. No. 12/625,510, Office Action dated Dec. 1, 2011.
U.S. Appl. No. 12/628,173, Advisory Action dated Sep. 17, 2012.
U.S. Appl. No. 12/628,173, Office Action dated Jan. 16, 2014.
U.S. Appl. No. 12/628,173, Office Action dated Jun. 11, 2012.
U.S. Appl. No. 12/628,173, Office Action dated Jun. 21, 2013.
U.S. Appl. No. 12/628,173, Office Action dated Nov. 8, 2011.
U.S. Appl. No. 12/628,177, Office Action dated Aug. 20, 2012.
U.S. Appl. No. 12/628,177, Office Action dated Mar. 18, 2013.
U.S. Appl. No. 12/628,177, Office Action dated Mar. 29, 2012.
U.S. Appl. No. 12/628,177, Office Action dated Nov. 9, 2011.
U.S. Appl. No. 12/628,198, Office Action dated Mar. 19, 2013.
U.S. Appl. No. 12/628,198, Office Action dated Aug. 20, 2012.
U.S. Appl. No. 12/628,198, Office Action dated Mar. 29, 2012.
U.S. Appl. No. 12/628,198, Office Action dated Nov. 8, 2011.
U.S. Appl. No. 12/628,201, Office Action dated Aug. 20, 2012.
U.S. Appl. No. 12/628,201, Office Action dated Mar. 14, 2013.
U.S. Appl. No. 12/628,201, Office Action dated Mar. 28, 2012.
U.S. Appl. No. 12/628,201, Office Action dated Nov. 10, 2011.
U.S. Appl. No. 12/628,203, Office Action dated Aug. 21, 2012.
U.S. Appl. No. 12/628,203, Office Action dated Mar. 14, 2013.
U.S. Appl. No. 12/628,203, Office Action dated Mar. 28, 2012.
U.S. Appl. No. 12/628,203, Office Action dated Nov. 10, 2011.
U.S. Appl. No. 12/628,210, Office Action dated Aug. 21, 2012.
U.S. Appl. No. 12/628,210, Office Action dated Mar. 20, 2013.
U.S. Appl. No. 12/628,210, Office Action dated Mar. 28, 2012.
U.S. Appl. No. 12/628,210, Office Action dated Nov. 14, 2011.
U.S. Appl. No. 13/730,696, Office Action dated Jul. 6, 2015.
U.S. Appl. No. 14/133,635, Office Action dated Feb. 11, 2016.
U.S. Appl. No. 14/133,635, Office Action dated Jul. 26, 2016.
U.S. Appl. No. 14/133,635, Office Action dated Nov. 16, 2016.

(56) References Cited

OTHER PUBLICATIONS

U.S. Appl. No. 14/133,635, Office Action dated Mar. 7, 2017.
U.S. Appl. No. 14/133,635, Advisory Action dated Jul. 6, 2017.
U.S. Appl. No. 14/133,635, Office Action dated Aug. 25, 2017.
U.S. Appl. No. 15/985,615, Office Action dated Jul. 27, 2018.
U.S. Appl. No. 15/985,615, Office Action dated Mar. 7, 2019.
Velho, G., et al., "Strategies for Calibrating a Subcutaneous Glucose Sensor", Biomedica Biochimica Acta, vol. 48, 1989, pp. 957/964.
Wilson, G. S., et al., "Progress Toward the Development of an Implantable Sensor for Glucose", Clinical Chemistry, vol. 38, No. 9, 1992, pp. 1613/1617.

* cited by examiner

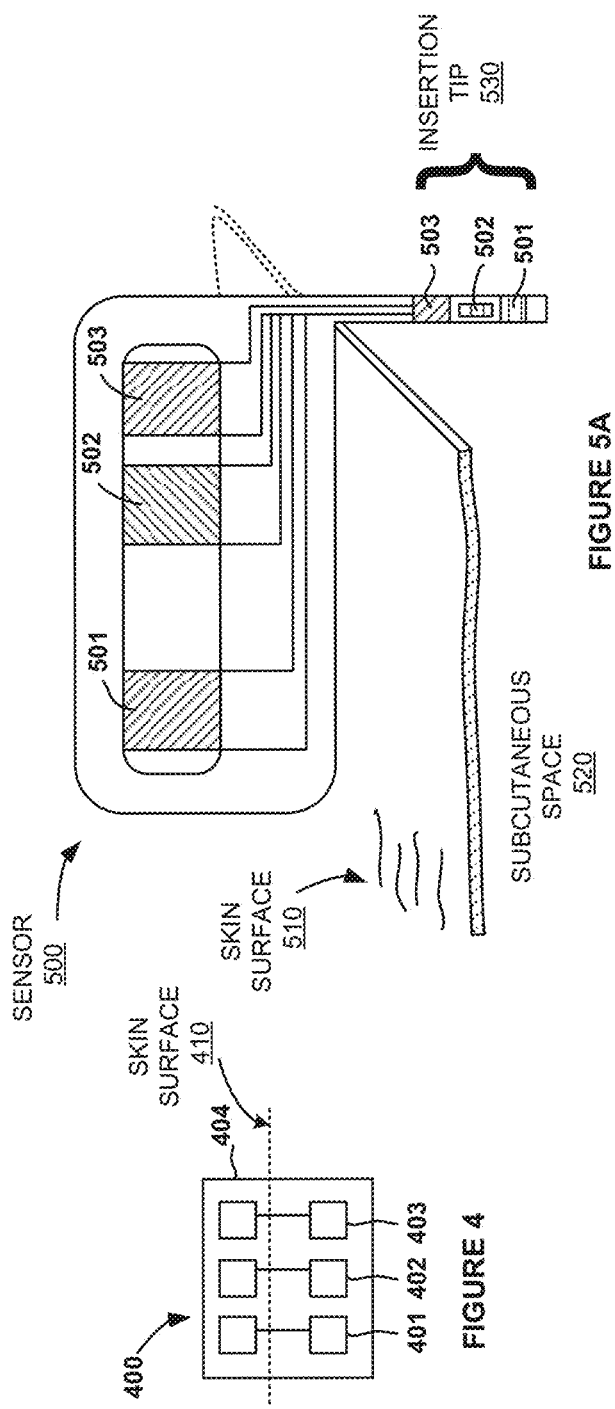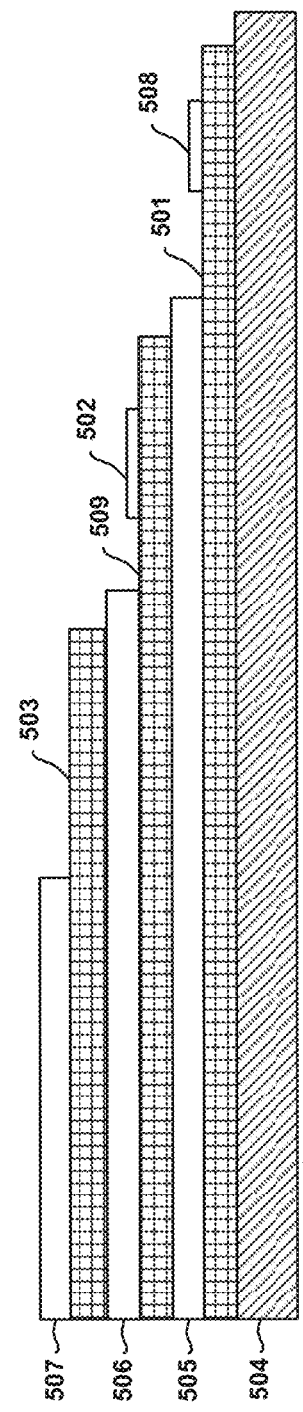

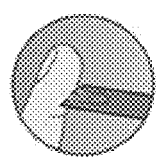 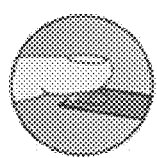 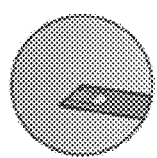 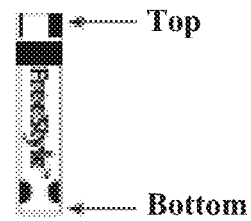
FIGURE 6            FIGURE 7
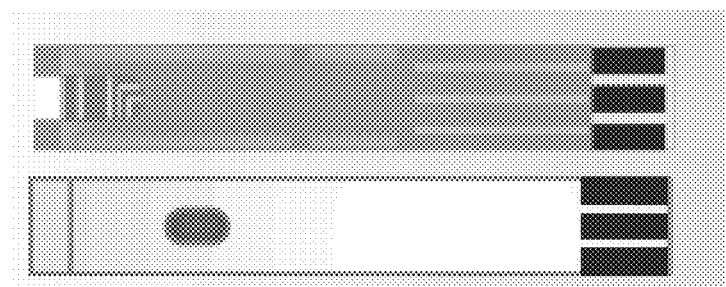
FIGURE 8
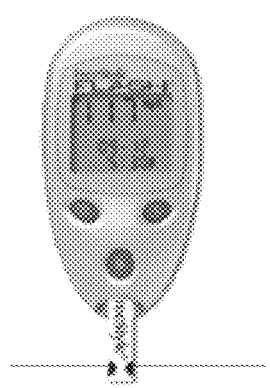            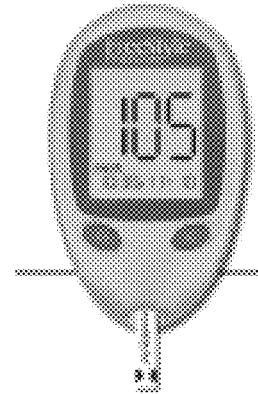
FIGURE 9            FIGURE 10

|  | System A | System B | System C | System D | System E |
|---|---|---|---|---|---|
| Description | Retrospective for HCP Only | Real-Time, 1-way, Wired | Real-time, 1-way, Wireless | Data Logger, wired | Real-time, 2-way, wireless |
| Data | Retrospective | Prospective | Prospective | Retrospective | Prospective |
| BGM | Existing devices | Existing devices | Modified BGM | CGM/ BGM | CGM/ BGM |
| Receiver | Blinded, Assessor | Assessor | Assessor | Embedded in Meter | Embedded in RF Module |
| Transmitter/ Sensor | Transmitter/ Sensor | Transmitter/ Sensor | Transmitter/ Sensor | Data Logger | Transmitter/ Sensor |
| Data Management | DMS | DMS | DMS | DMS | DMS |
| Transmission | BGM ▲ Cable ▲ PC RX ▲ Bluetooth ▲ PC | BGM ▲ Cable ▲ Receiver RX ▲ Bluetooth ▲ PC | BGM ▲ Wireless Adapter ▲ Receiver RX ▲ Bluetooth ▲ PC | Data logger ▲ Cable or Wireless ▲ Meter | Data logger ▲ Wireless adapter ▲ BGM |

FIGURE 16

HEALTH MANAGEMENT DEVICES AND METHODS

RELATED APPLICATIONS

The present application is a continuation of Ser. No. 17/019,122 filed Sep. 11, 2020, which is a continuation of U.S. patent application Ser. No. 16/032,017 filed Jul. 10, 2018, which is a continuation of U.S. patent application Ser. No. 14/094,719 filed Dec. 2, 2013, which is a continuation of U.S. patent application Ser. No. 12/143,731 filed Jun. 20, 2008, now U.S. Pat. No. 8,597,188, which claims priority to U.S. Provisional Application No. 60/945,579 filed Jun. 21, 2007, entitled "Health Management Devices and Methods" and assigned to the assignee of the present application, Abbott Diabetes Care Inc., the disclosures of each of which are incorporated by reference for all purposes.

BACKGROUND

The detection of the level of analytes, such as glucose, lactate, oxygen, and the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Accordingly, of interest are devices that allow a user to test for one or more analytes.

SUMMARY

In accordance with embodiments of the present disclosure, there is provided analyte monitoring methods and system for prospective or retrospective data analysis and processing including an in vivo analyte monitoring system comprising an analyte sensor and a module to collect analyte data from the sensor for use by a first user, a data management system to manipulate analyte data at a remote site, the analyte data transferred to the data management system from the in vivo system, where the system is configured for use by at least a second user, and further where there is provided a patient privacy system to limit or restrict data access by the type of users.

BRIEF DESCRIPTION OF THE DRAWINGS

FIG. 4 shows a schematic diagram of an embodiment of an analyte sensor according to the present disclosure;

FIGS. 5A-5B show a perspective view and a cross sectional view, respectively of another embodiment an analyte sensor;

FIGS. 6-10 illustrate exemplary blood glucose meters and test strips using the same;

FIG. 16 shows a table of exemplary embodiments and respective features in one embodiment.

DETAILED DESCRIPTION

Figure 1:
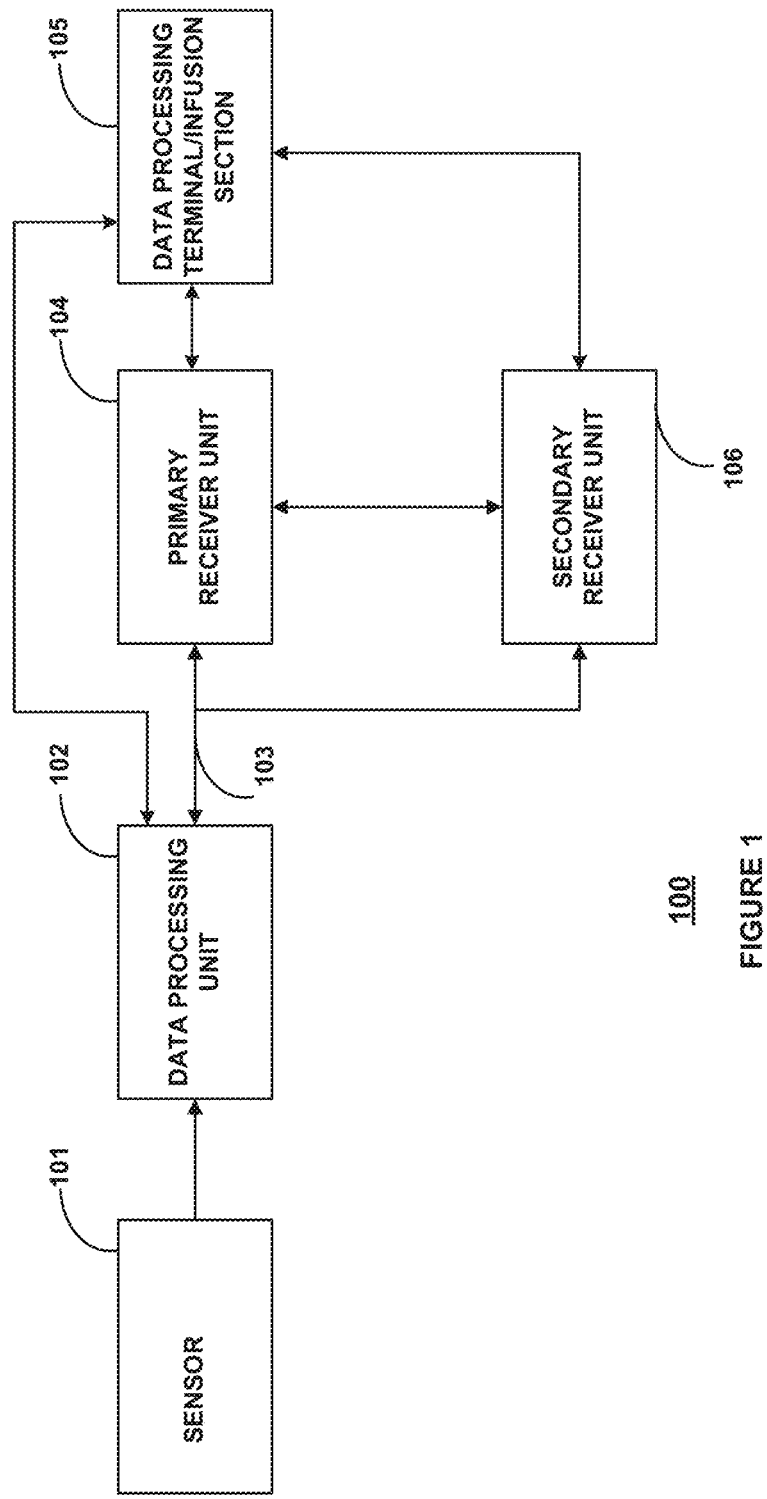
FIG. 1 shows a block diagram of an embodiment of a data monitoring and management system according to the present disclosure.

Before the present disclosure is described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and a BG meter system.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise.

The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Analyte sensors that do not require bodily fluid contact are also contemplated. Embodiments of the analyte sensors may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time to, the rate of change of the analyte, etc. Predictive alarms may notify the user of a predicted analyte level that may be of concern in advance of the user's analyte level reaching the future level. This provides the user an opportunity to take corrective action.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Analytes that may be monitored include, but are not limited to acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit or control unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or a bi-directional communication device. A docking cradle may recharge a power supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit may include a fixation element such as adhesive or the like to secure it to the user's body. A mount (not shown) attachable to the user and mateable with the unit 102 may be used. For example, a mount may include an adhesive surface. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In certain embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1, may use one or more of: an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Figure 2:
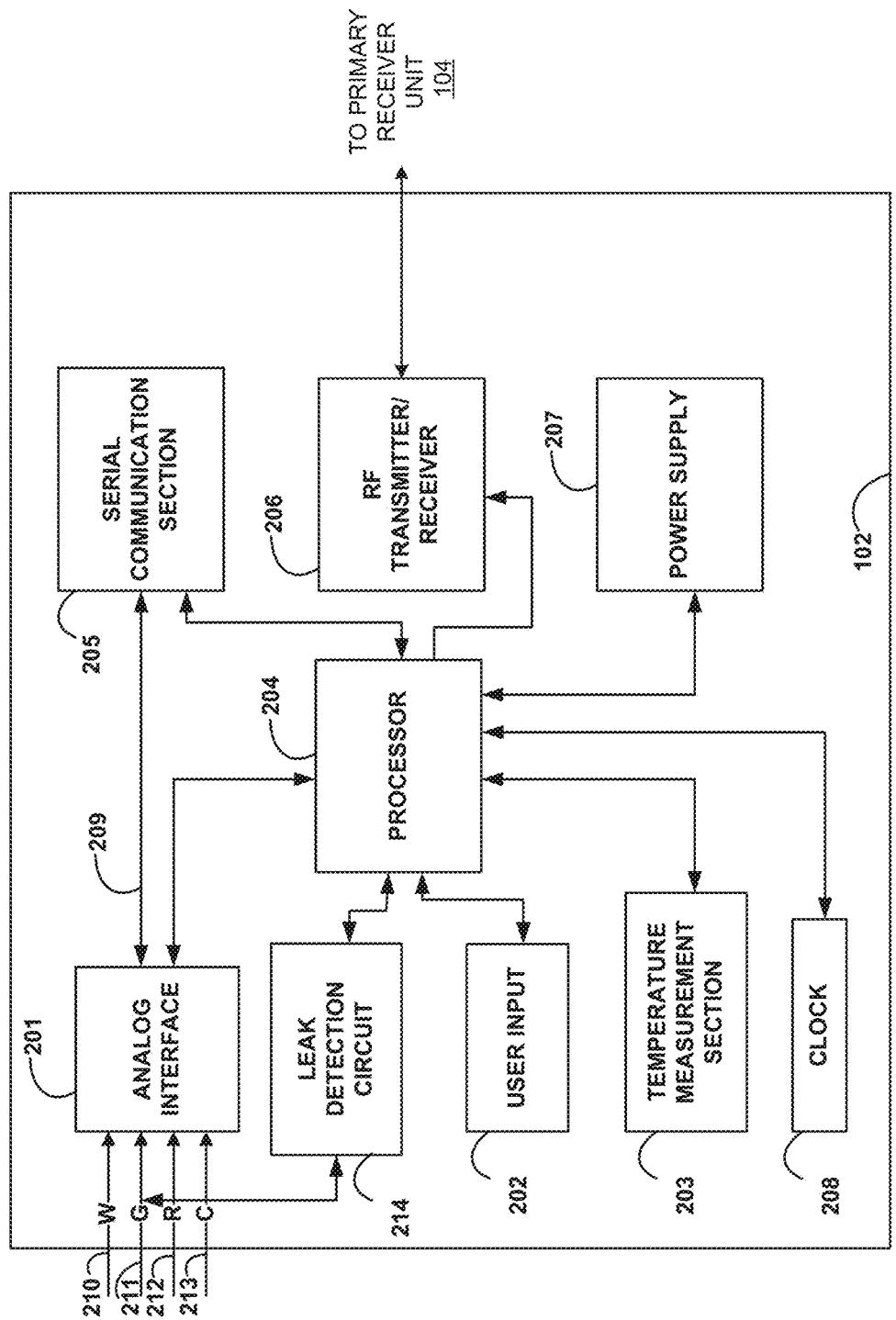
FIG. 2 shows a block diagram of an embodiment of the transmitter unit of the data monitoring and management system of FIG. 1.

FIG. 2 shows a block diagram of an embodiment of a data processing unit of the data monitoring and detection system shown in FIG. 1. User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers. Referring to the Figure, the data processing unit 102 in one embodiment includes an analog interface 201 configured to communicate with the sensor 101 (FIG. 1), a user input 202, and a temperature measurement section 203, each of which is operatively coupled to a processor 204 such as a central processing unit (CPU).

As can be seen in the embodiment of FIG. 2, the sensor 101 (FIG. 1) includes four contacts, three of which are electrodes—work electrode (W) 210, reference electrode (R) 212, and counter electrode (C) 213, each operatively coupled to the analog interface 201 of the data processing unit 102. This embodiment also shows optional guard contact (G) 211. Fewer or greater electrodes may be employed. For example, the counter and reference electrode functions may be served by a single counter/reference electrode, there may be more than one working electrode and/or reference electrode and/or counter electrode, and so on. The processor shown in FIG. 2 may be equipped with sufficient memory to store the data of interest (such as analyte data) for extended periods of time ranging from one to several samples to the number of samples obtained for an entire wear period of several days to weeks. In one aspect, the memory may be included as part of the processor 204. In another embodiment, a separate memory unit such as a memory chip, random access memory (RAM) or any other storage device for storing for subsequent retrieval data. The electronics of the on-skin sensor control unit and the sensor are operated using a power supply 207, e.g., a battery. Additionally, as can be seen from the Figure, clock 208 is provided to, among others, supply real time information to the processor 204. In one embodiment, a unidirectional input path is established from the sensor 101 (FIG. 1) and/or manufacturing and testing equipment to the analog interface 201 of the data processing unit 102, while a unidirectional output is established from the output of the RF transmitter 206 of the data processing unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. Also shown is a leak detection circuit 214 coupled to the guard contact (G) 211 and the processor 204 in the data processing unit 102. The leak detection circuit 214 in accordance with one embodiment of the present invention may be configured to detect leakage current in the sensor 101 to determine whether the measured sensor data are corrupt or whether the measured data from the sensor 101 is accurate.

Figure 3:
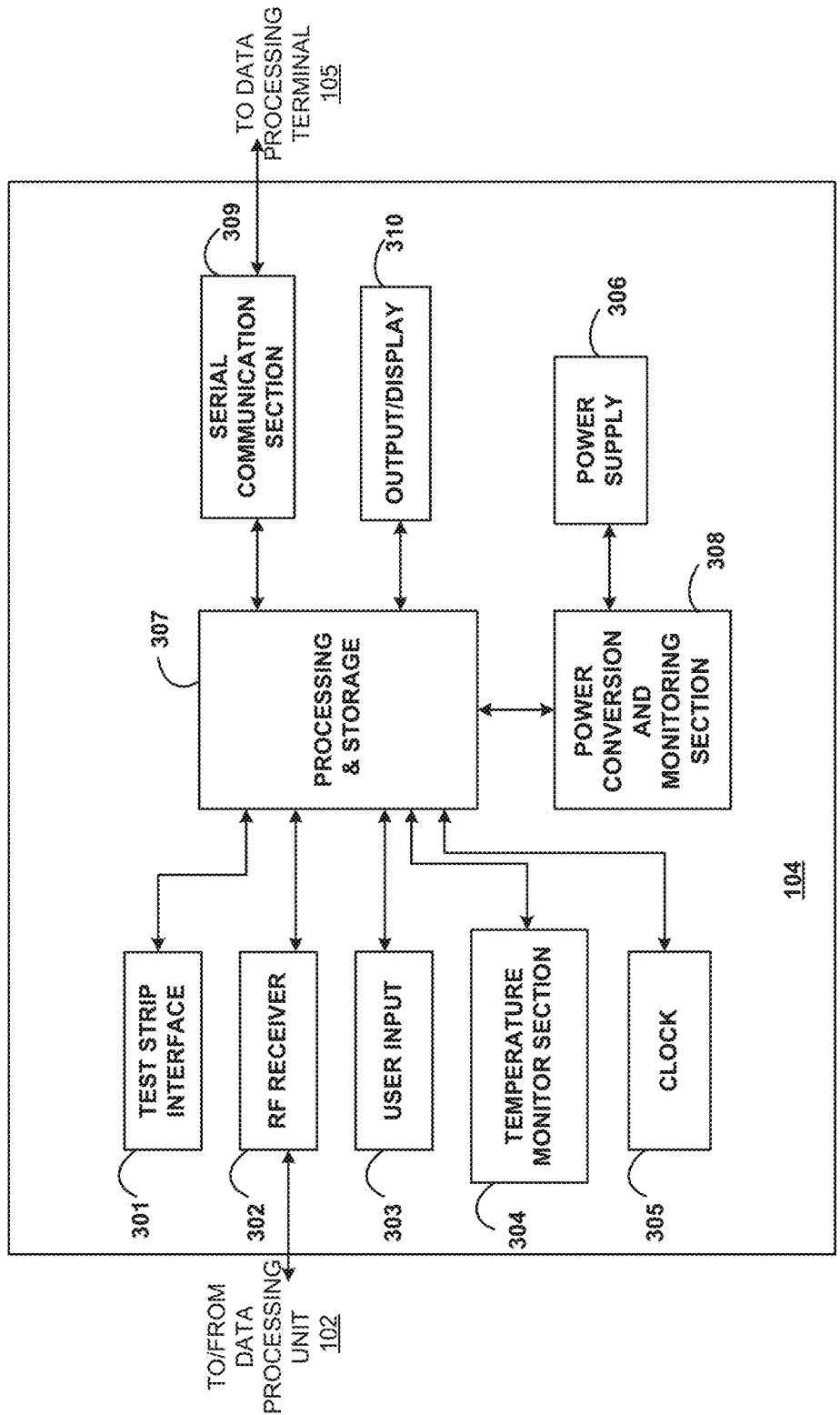
FIG. 3 shows a block diagram of an embodiment of the receiver/monitor unit of the data monitoring and management system of FIG. 1.

FIG. 3 is a block diagram of an embodiment of a receiver/monitor unit such as the primary receiver unit 104 of the data monitoring and management system shown in FIG. 1. The primary receiver unit 104 includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments, the test strip interface 301 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care Inc. Glucose information obtained by the in vitro glucose testing device may be used for a variety of purposes, computations, etc. For example, the information may be used to calibrate sensor 101, confirm results of the sensor 101 to increase the confidence thereof (e.g., in instances in which information obtained by sensor 101 is employed in therapy related decisions), and the like.

Figure 12:
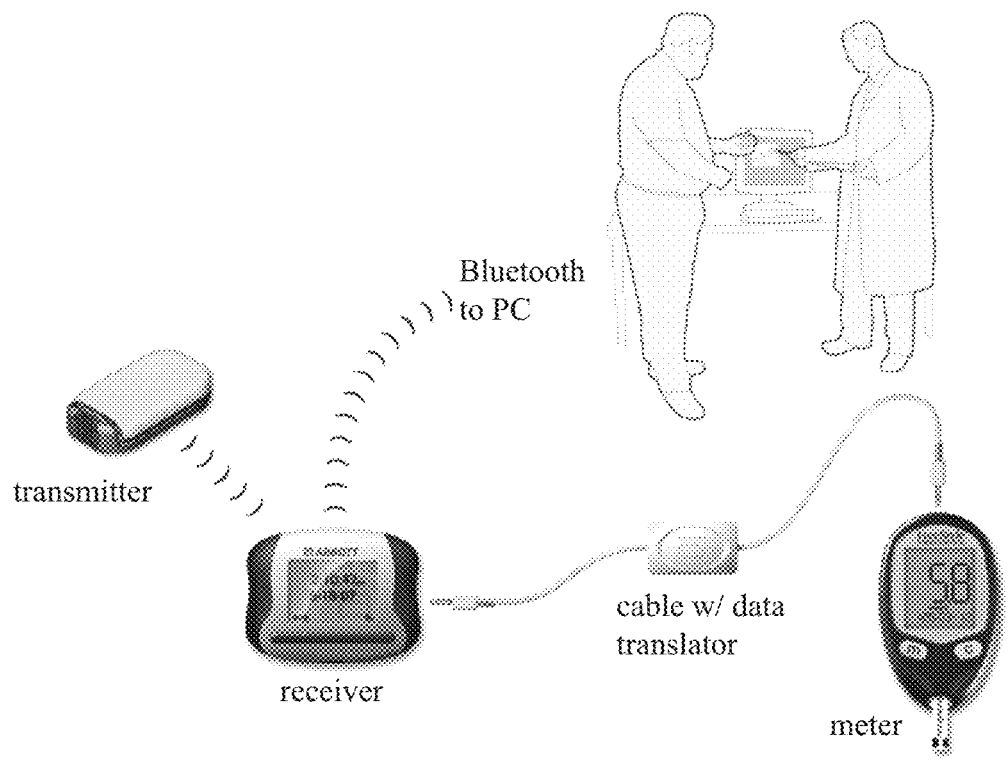
FIG. 12 illustrates prospective calibration of an assessor (AS) data, and unblinded assessor (AS) data in one embodiment.

In further embodiments, the data processing unit 102 and/or the primary receiver unit 104 and/or the secondary receiver unit 106, and/or the data processing terminal/infusion section 105 may be configured to receive the blood glucose value wirelessly (or via a wire as shown in FIG. 12) over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in one or more of the data processing unit 102, the primary receiver unit 104, secondary receiver unit 106, or the data processing terminal/infusion section 105.

Additional detailed description of embodiments of test strips, blood glucose (BG) meters and continuous monitoring systems and data management systems that may be employed are provided in but not limited to: U.S. Pat. Nos. 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; U.S. patent application Ser. No. 10/745,878 filed Dec. 26, 2003, now U.S. Pat. No. 7,811,231 entitled "Continuous Glucose Monitoring System and Methods of Use", and elsewhere, the disclosures of each which are incorporated herein by reference for all purposes.

FIG. 4 schematically shows an embodiment of an analyte sensor in accordance with the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 510, 502 and 503, of the sensor 500 as well as the substrate and the dielectric layers are provided in a layered configuration or construction. For example, as shown in FIG. 5B, in one aspect, the sensor 500 (such as the sensor 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

A first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, and in one aspect, may include a layer of silver/silver chloride (Ag/AgCl), gold, etc.

A second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer). The embodiment of FIGS. 5A and 5B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments, one or more of the electrodes 501, 502, 503 may be disposed on opposing sides of the substrate 504. In such embodiments, contact pads may be on the same or different sides of the substrate. For example, an electrode may be on a first side and its respective contact may be on a second side, e.g., a trace connecting the electrode and the contact may traverse through the substrate.

As noted above, analyte sensors may include an analyte-responsive enzyme to provide a sensing component or sensing layer. Some analytes, such as oxygen, can be directly electro oxidized or electro reduced on a sensor, and more specifically at least on a working electrode of a sensor. Other analytes, such as glucose and lactate, require the presence of at least one electron transfer agent and/or at least one catalyst to facilitate the electro oxidation or electro reduction of the analyte. Catalysts may also be used for those analytes, such as oxygen, that can be directly electro oxidized or electro reduced on the working electrode. For these analytes, each working electrode includes a sensing layer (see for example sensing layer 508 of FIG. 5B) proximate to or on a surface of a working electrode. In many embodiments, a sensing layer is formed near or on only a small portion of at least a working electrode.

The sensing layer includes one or more components designed to facilitate the electrochemical oxidation or reduction of the analyte. The sensing layer may include, for example, a catalyst to catalyze a reaction of the analyte and produce a response at the working electrode, an electron transfer agent to transfer electrons between the analyte and the working electrode (or other component), or both.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided).

A sensing layer that is in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electro oxidation of the glucose, lactate, or oxygen, respectively.

In other embodiments the sensing layer is not deposited directly on the working electrode. Instead, the sensing layer 508 may be spaced apart from the working electrode, and separated from the working electrode, e.g., by a separation layer. A separation layer may include one or more membranes or films or a physical distance. In addition to separating the working electrode from the sensing layer the separation layer may also act as a mass transport limiting layer and/or an interferent eliminating layer and/or a biocompatible layer.

In certain embodiments which include more than one working electrode, one or more of the working electrodes may not have a corresponding sensing layer, or may have a sensing layer which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electro reducible and electro oxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes such as ferrocene. Examples of inorganic redox species are hexacyanoferrate (III), ruthenium hexamine etc.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, such as 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase or oligosaccharide dehydrogenase, flavine adenine dinucleotide (FAD) dependent glucose dehydrogenase, nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer (Abbott Diabetes Care Inc.) that works at a gentle oxidizing potential, e.g., a potential of about +40 mV. This sensing layer uses an osmium (Os)-based mediator designed for low potential operation and is stably anchored in a polymeric layer. Accordingly, in certain embodiments the sensing element is redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating, etc.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e. reduction of the flux of analyte that can reach the sensing layer, (2) biocompatibility enhancement, or (3) interferent reduction.

The description herein is directed primarily to electrochemical sensors for convenience only and is in no way intended to limit the scope of the disclosure. Other sensors and sensor systems are contemplated. Such include, but are not limited to, optical sensors, colorimetric sensors, and sensors that detect hydrogen peroxide to infer glucose levels, potentiometric sensors, coulometric sensors, or oxygen sensors.

For example, a hydrogen peroxide-detecting sensor may be constructed in which a sensing layer includes enzyme such as glucose oxides, glucose dehydrogenase, or the like, and is positioned proximate to the working electrode. The sending layer may be covered by a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from a sensing layer prepared by crosslinking two components together, for example: (1) a redox compound such as a redox polymer containing pendent Os polypyridyl complexes with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing layer is constructed by crosslinking together (1) a redox polymer containing pendent Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

A sensor may also include an active agent such as an anticlotting and/or antiglycolytic agent(s) disposed on at least a portion a sensor that is positioned in a user. An anticlotting agent may reduce or eliminate the clotting of blood or other body fluid around the sensor, particularly after insertion of the sensor. Examples of useful anticlotting agents include heparin and tissue plasminogen activator (TPA), as well as other known anticlotting agents. Embodiments may include an antiglycolytic agent or precursor thereof. Examples of antiglycolytic agents are glyceraldehyde, fluoride ion, and mannose.

Sensors may be configured to require no system calibration or no user calibration. For example, a sensor may be factory calibrated and may not require further calibration during the life of the sensor. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

Calibration may be accomplished using an in vitro test strip (or other reference), e.g., a small sample test strip such as a test strip that requires less than about 1 microliter of sample (for example FreeStyle® blood glucose monitoring test strips from Abbott Diabetes Care Inc.). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combine with data obtained from previous calibration events, e.g., averaged including weighted averaged, etc., to calibrate. In certain embodiments, a system need only be calibrated once by a user, where recalibration of the system is not required.

Analyte systems may include an optional alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels approach, reach or exceed a threshold value. An alarm system may also, or alternatively, be activated when the rate of change, or acceleration of the rate of change, in analyte level increase or decrease approaches, reaches or exceeds a threshold rate or acceleration. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The subject disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

In certain embodiments, a continuous glucose ("CG") monitoring system (for example a FreeStyle Navigator® continuous glucose monitoring system or certain components thereof) may be used to assess diabetes and treatment options, e.g., assessed by a health care provider ("HCP") device. Such an assessment may occur at initial phases of, or at the beginning of diagnosis or onset of, diabetic condition. A CG system may be provided to a user to monitor glucose levels for a period of time, e.g., about one day to about one month or more, e.g., about a few days to about a few weeks, e.g., about 1-2 weeks. The information gathered by the CG system may be reviewed retrospectively by an HCP, e.g., stored in an HCP device memory and communicated to (including transferred to) HCP, to assess the next steps of treating and/or monitoring the user's glucose levels to control diabetes. These CG systems may generally be referred to as "assessor" ("AS") systems. Generally, a CG system is an in vivo system, e.g., that a user may borrow/rent/otherwise obtain whenever they are collecting glucose data.

In certain embodiments, an HCP may use AS system data obtained from a user to assess whether the user would benefit from using an in vitro meter (test strip and meter, including an integrated glucose monitoring system). The HCP may then prescribe such a system for the user. Of course, an HCP may determine that the user continue to use an in vivo system or that no additional glucose monitoring is required. In many embodiments, an HCP may determine (and prescribe) a short assay time/small sample size in vitro system, and a user may monitor their glucose levels using such a system. Accordingly, after using an AS system to monitor glucose levels for a period of time, an HCP may, after reviewing the AS data obtained during this time, recommend that the user to continue to monitor glucose levels using an in vitro system. Typically (though not always) the user may use the in vitro system as the primary and sole source of glucose monitoring, i.e., the AS system need not be used by the user any longer, or may be used periodically.

In certain embodiments, a given AS system may be used to monitor glucose levels of a first person, an HCP may review the data therefrom, and the AS system may then be used by at least a second person (excluding the analyte sensor).

As noted above, an HCP may recommend (and prescribe) an in vitro system for a user if AS data reviewed by the HCP after being used for a period of time indicates that such a system would be beneficial for the user/patient.

Embodiments include devices which allow diabetics or users evaluating whether they have diabetes to measure the blood (or other bodily fluid) glucose levels, e.g., hand-held electronic meters (blood glucose meters), e.g., such as Freestyle® or Precision® blood glucose monitoring systems available from Abbott Diabetes Care Inc., of Alameda, Calif. which receives blood samples via enzyme-based test strips. Typically, a user inserts a test strip into a meter and lances a finger or alternate body site to obtain a blood sample. The drawn sample is applied to the test strip and the meter reads the strip and determines analyte concentration, which is then conveyed to the user. For example, a blood glucose meter may convert a current generated by the enzymatic reaction in the test strip to a corresponding blood glucose value which is displayed or otherwise provided to the patient to show the level of glucose at the time of testing. Such periodic discrete glucose testing helps diabetic patients to take any necessary corrective actions to better manage diabetic conditions.

Test strips for use with such in vitro systems may be adapted to measure the concentration of an analyte in any volume of sample, including but not limited to small volumes of sample, e.g., about 1 microliter or less sample, for example about 0.5 microliters or less, for example about 0.3 microliters or less, for example about 0.1 microliters or less. In some embodiments, the volume of sample may be as low as about 0.05 microliters or as low as about 0.03 microliters. Strips may be configured so that an accurate analyte measurement may be obtained using a volume of sample that wholly or partially fills a sample chamber of a strip. In certain embodiments, a test may only start when sufficient sample has been applied to a strip, e.g., as detected by a detector such as an electrode. An in vitro system may be programmed to allow re-application of additional sample if insufficient sample is firstly applied, e.g., the time to reapply sample may range from about 10 seconds to about 2 minutes, e.g., from about 30 seconds to about 60 seconds.

Strips may be side fill, front fill, top fill or corner fill, or any combination thereof. Test strips may be calibration-free, e.g., minimal input (if any) is required of a user to calibrate. In certain embodiments, no calibration test strips may be employed. In such embodiments, the user need not take any action for calibration, i.e., calibration is invisible to a user.

As noted above, strips are used with meters. In certain embodiments, meters may be integrated meters, i.e., a device which has at least one strip and at least a second element, such as a meter and/or a skin piercing element such as a lancet or the like, in the device. In some embodiments, a strip may be integrated with both a meter and a lancet, e.g., in a single housing. Having multiple elements together in one device reduces the number of devices needed to obtain an analyte level and facilitates the sampling process. For example, embodiments may include a housing that includes one or more analyte test strips, a skin piercing element and a processor for determining the concentration of an analyte in a sample applied to the strip. A plurality of strips may be retained in a magazine in the housing interior and, upon actuation by a user, a single strip may be dispensed from the magazine so that at least a portion extends out of the housing for use.

Test strips may be short test time test strips. For example, test times may range from about 1 second to about 20 seconds, e.g., from about 3 seconds to about 10 seconds, e.g., from about 3 seconds to about 7 seconds, e.g., about 5 seconds or about 3 seconds.

Exemplary meters and test strips and using the same are shown in FIGS. 6-10.

In certain embodiments, the glucose levels obtained by the AS system may not be displayed or otherwise communicated to a user in real time, i.e., the user of the system will be blinded to the data obtained—at least in real time. Stated otherwise, no glucose results are shown on the AS system. The AS data will thus be retrospective providing blind data, and will include a device (wired or wireless) so that an HCP device may download retrospective continuous glucose monitoring system data from the AS system for review and analysis. In certain embodiments, the AS system will not be calibrated in real time, e.g., will not include (or will not include a functional or the strip port will be blocked) strip port to accept a calibration test strip. An in vitro system may be used concurrently with the system, and the data obtained by the in vitro system reviewed and used in the review and/or processing of AS data. For example, the in vitro data may be used to retrospectively calibrate the CG data, e.g., at a remote site such as an HCP site, and as shown, for example, in FIG. 11.

Figure 11:
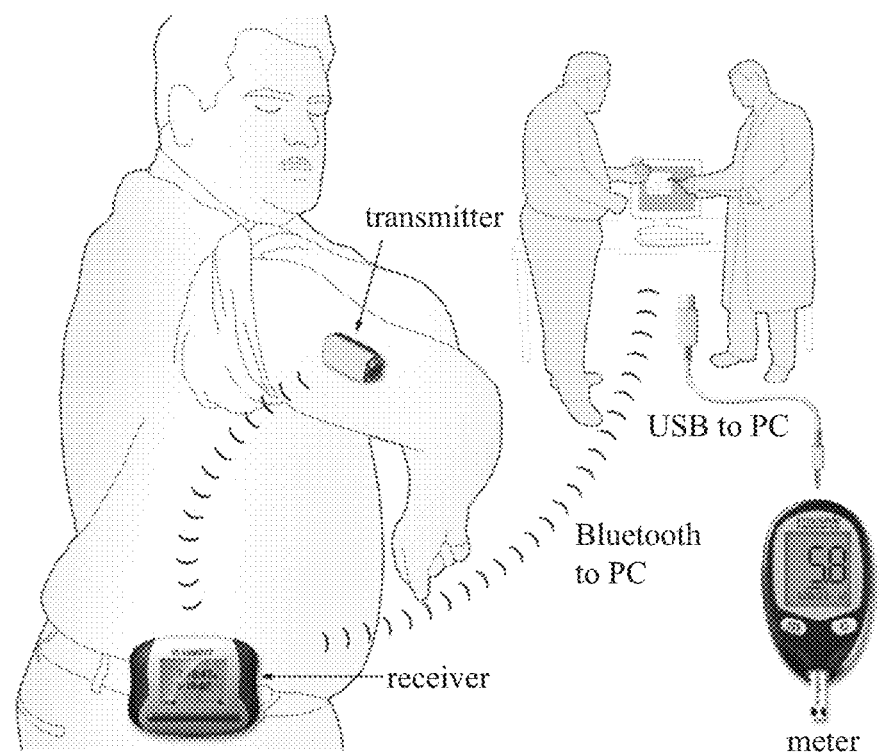
FIG. 11 illustrates in vitro data transfer to a health care provider (HCP) via Universal Serial Bus (USB) connection to a computing device such as a personal computer (PC) in one embodiment.

Referring to FIG. 11, in one aspect, a user wears and uses an AS system that includes an in vivo analyte sensor (not shown) coupled to an AS data processing unit (transmitter) worn (in this embodiment) on the user's arm, and an AS receiver unit to receive information from the AS data processing unit (wired or wirelessly). A blood glucose ("BG") or in vitro meter (used interchangeably) is also used and is configured to transfer data to a remote site such as shown here an HCP PC terminal (either wirelessly or otherwise). Also included is a data management system ("DMS"). There is no data transfer connection between the in vitro meter and the AS system, data transfer exists between the AS system and a DMS, such as a PC-based DMS.

In the particular embodiment of FIG. 11, in vitro data is transferred to the HCP PC terminal via USB connection. The PC terminal may be at the user's location, at which the data may then be accessed by the HCP (e.g., via a network connection, server connection or otherwise), or downloaded to a computing device at the remote location. Once the HCP collects AS data (which may be transferred to the HCP as raw data or may be processed at least in certain respects), the data may be reviewed and/or further processed. For example, the AS data may be calibrated using the collected in vitro data. The calibrated AS data may then be reviewed and/or processed further. For example, reports may be generated. A data management system may be employed, e.g., such as the CoPilot™ data management system available from Abbott Diabetes Care Inc., or analogous system. The HCP PC terminal may generate and review reports produced using the AS data.

Accordingly, in certain embodiments an HCP attaches the AS processing unit with transmitter to the user at the HCP office and provides a reusable receiver unit to the user. The user may wear and collect data with the AS receiver and transmitter for about one or more days, e.g., about 2-30 days, e.g., about 3-7 days, e.g., about 5-7 days. The user performs BG tests on their in vitro meter at appropriate times, e.g., at 1, 2, 10, 24 and/or 72 hours after AS sensor insertion in certain embodiments. The user brings the AS receiver unit and in vitro meter to the HCP office and the HCP connects the in vitro meter via a USB cable (or otherwise including wirelessly) to a computing device such as the PC terminal and downloads the in vitro data from the meter's memory. The AS receiver wirelessly (or otherwise) transmits data to the PC. The HCP may view the AS and/or BG information using a DMS loaded and running on the HCP PC terminal.

In one aspect, the data obtained by the in vitro meter includes a time stamp based, for example, from an internal clock. The in vitro meter in one aspect may be synchronized with the clock of the PC terminal so that when the time stamped blood glucose values are received from the in vitro meter, the time of day information associated with each blood glucose test and the resulting blood glucose values are time synchronized with the corresponding analyte data in the PC terminal for further processing and analysis. In this manner, improved accuracy may be obtained. Further, the transmitted blood glucose values from the in vitro meter may also be associated with the unique identifier of the in vitro meter. In this manner, each blood glucose value derived or obtained from the in vitro meter will identify the corresponding in vitro meter based on its unique identifier.

In this manner, in one aspect, the user may be provided with limited or no real time data from the AS receiver during the time the glucose data is collected from the user. As such, user behavior or health care or treatment based decisions are limited or avoided by not allowing the user to view the on-going continuous glucose level monitored by the AS sensor and collected by the AS system. In one aspect, the AS system may be configured to provide limited output information to the user during the data collection modes, such as an indication that the AS system is functioning properly (for example, with periodic audible alerts, visual displays indicating system integrity, and the like). Other information may likewise be displayed or output on the AS receiver to the user such as, for example, the time of day information, the duration of the data collection elapsed, and so on.

Certain embodiments include prospective calibration of AS data, and unblinded AS data. An exemplary embodiment of such a system is shown in FIG. 12. This embodiment includes an AS data processing unit that includes a transmitter worn and used by a user, an AS receiving unit, an in vitro meter capable of transferring data to the AS system, (herein shown using a wired connection, but wireless may also be used), and a DMS. Accordingly, in this embodiment, glucose results of the AS system are communicated to the user in real-time, e.g., audibly and/or visually such as on a display. There is unidirectional transfer of data from the in vitro blood glucose meter to the AS receiver, e.g., using a USB cable or the like. In certain embodiments, the transfer of data may be bidirectional so the BG meter could (for example) display the most recent CG data. This would greatly enhance the value of the BG meter (to be able to display glucose data without the pain of drawing the blood), and more generally the BG meter may be used as a display unit for medical data besides just BG. For example, this may be included in a Data Logger embodiment. The embodiment of FIG. 12 can be configured to show or not show ("blind") CG data since it uses prospective data.

Accordingly, in certain embodiments an HCP attaches the AS processing unit with transmitter to a user at the HCP office and provides a loaner or reusable AS receiver. The user may wear and collect data with the AS receiver and transmitter for about one or more days, e.g., about 2-30 days, e.g., about 3-7 days, e.g., about 5-7 days. The user performs BG tests on their in vitro meter at appropriate times, e.g., at 10, 24 and 72 hours after AS sensor insertion in certain embodiments. When the user performs a BG test on their in vitro meter, the user couples (wired or wirelessly) the meter to the AS receiver. The AS receiver may be calibrated using this transferred BG data. The user brings the AS receiver and in vitro meter to the HCP office. The AS receiver wirelessly (or otherwise) transmits data to the PC. The HCP may view the AS and/or BG information using a DMS.

Figure 13:
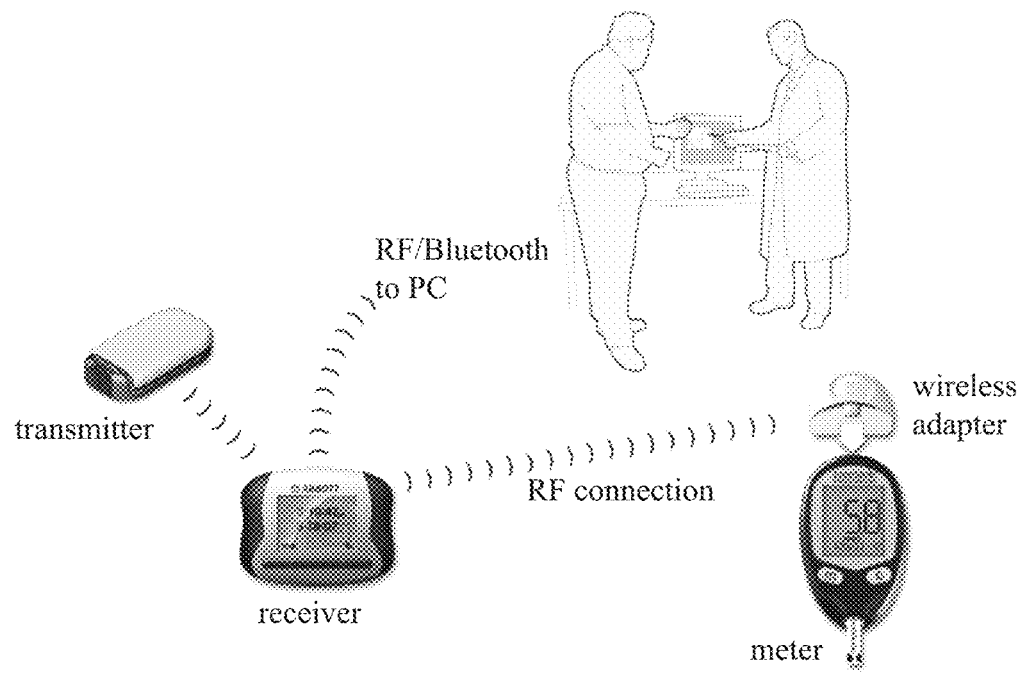
FIG. 13 illustrates prospective calibration of the assessor (AS) data, unblinded data and associated analysis and an RF module in one embodiment.

Certain embodiments include prospective calibration of AS data, unblinded data and an RF module. An exemplary embodiment of such a system is shown in FIG. 13. This embodiment includes an AS data processing unit that includes a transmitter worn and used by a user, an AS receiving unit, an in vitro meter capable of transferring data to the AS system, herein shown using a wired connection, (but wireless may also be used), an RF module, and a DMS. Accordingly, in this embodiment glucose results of the AS system are communicated to the user in real-time, e.g., audibly and/or visually such as on a display. As shown, there is unidirectional transfer of data from the in vitro blood glucose meter to the AS receiver, e.g., using RF and a wireless adaptor coupled to the in vitro meter. However, there may be bidirectional transfer of data that permits the in vitro meter to display AS data (i.e., the in vitro meter including functionality to output the continuous analyte sensor data).

Accordingly, in certain embodiments an HCP attaches the AS processing unit with transmitter to a user at the HCP office and provides a loaner or reusable AS receiver. The user may wear and collect data with the AS receiver and transmitter for about one or more days, e.g., about 2-30 days, e.g., about 3-7 days, e.g., about 5-7 days. The user performs BG tests on their in vitro meter at appropriate times, e.g., at 10, 24 and 72 hours after AS sensor insertion in certain embodiments. When the user performs a BG test on their in vitro meter, the wireless adapter will have to be coupled to the meter and the BG test data may be wirelessly sent to the AS receiver. The collected data in the AS receiver may be calibrated using this transferred BG data. The user brings the AS receiver and in vitro meter to the HCP office. The AS receiver wirelessly (or otherwise) transmits data to the PC. The HCP may view the AS data and/or BG information using a DMS.

Figure 14:
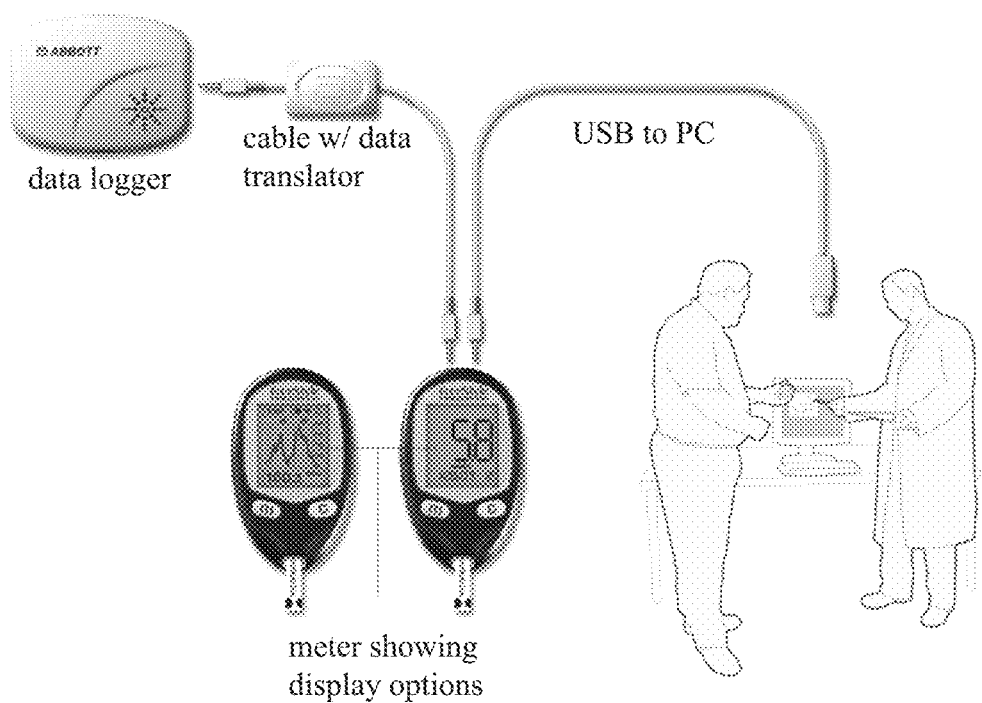
FIG. 14 illustrates unblinded, retrospective data and associated analysis and a USB connection in one embodiment.

Certain embodiments include unblinded, retrospective data and a USB cable. An exemplary embodiment of such a system is shown in FIG. 14. This embodiment includes a Data Logger, a USB cable, a serial cable to Data Logger and an enhanced BG meter having continuous glucose monitoring functionalities. Accordingly, in this embodiment continuous glucose monitoring capabilities are accorded with the in vitro meter, which includes a mini usb port. A user wears the Data Logger and may view the retrospective data obtained by the Data Logger on the in vitro meter. There is unidirectional transfer (wired or wireless) of data from Data Logger to the BG meter—or may be bidirectional to allow calibration of the CG data with BG data as well as to display CG data on the BG meter.

Accordingly, in certain embodiments an HCP attaches an in vivo sensor and Data Logger to a user at the HCP office. The user may wear and collect data with the Data Logger (for example, provided in the AS transmitter coupled to the in vivo sensor) for about one or more days, e.g., about 2-30 days, e.g., about 3-7 days, e.g., about 5-7 days. The user connects the USB cable from the Data Logger to the BG meter to download results. The user brings the BG meter to the HCP site and transits data, e.g., via usb cable, from the BG meter to the HCP PC or computer terminal. The HCP may view the Data Logger and/or BG information using a DMS.

Figure 15:
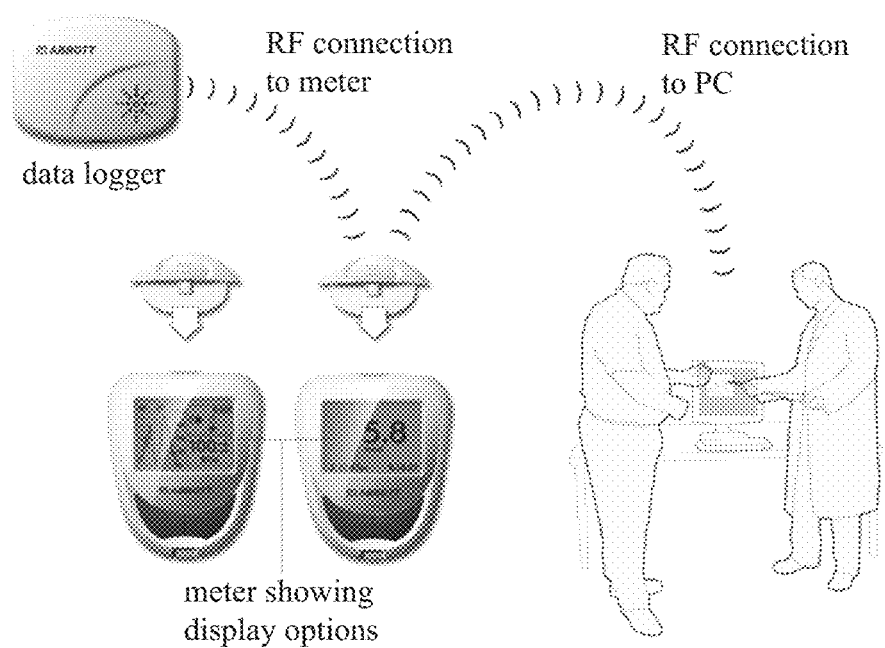
FIG. 15 illustrates unblinded, prospective data and associated analysis and a wireless adapter in one embodiment.

Certain embodiments include unblinded, prospective data and a wireless adapter. An exemplary embodiment of such a system is shown in FIG. 15. This embodiment includes a BG meter, an RF module and a Data Logger. The BG meter is an enhanced BG meter having continuous glucose monitoring functionalities and a USB port. A user wears a Data Logger and can view prospective data of the Data Logger on the BG meter. There is bidirectional transfer (wired or wireless) of data from Data Logger to the BG meter.

Accordingly, in certain embodiments an HCP attaches an in vivo sensor and Data Logger to a user at the HCP office. The user may wear and collect data with the Data Logger and transmitter for about one or more days, e.g., about 2-30 days, e.g., about 3-7 days, e.g., about 5-7 days. The user connects the wireless adapter to the BG meter to download results. The user brings the BG meter to the HCP site and transits data, e.g., via the wireless adapter, from the BG meter to the HCP pc. HCP may view the Data Logger and/or BG information using a DMS.

In certain embodiments, an AS receiver unit may be embedded in a BG meter. That is, the BG meter may be configured to directly communicate with the AS transmitter and to receive/store data from the AS transmitter and collect the monitored glucose levels from the in vivo sensor.

While in the embodiments described above, specific implementation of data communication including wired or cabled and wireless, and data processing is described, within the scope of the present disclosure, other data communication techniques may be used including wired over a cable connection and/or wireless over a communication link such as RF communication link, infrared communication link, Bluetooth® communication link, and the like, as well as networked data communication over data networks such as, but not limited to local area network, wide area network, metropolitan area network and the like, using data protocols such as, but not limited to TCP/IP, Internet Protocol version 4 (IPv4), Internet Protocol version 6 (IPv6), wireless application protocol (WAP), and the like.

FIG. 16 shows a table of exemplary embodiments and respective features that may be included. Any feature may be combined with any other embodiment, and/or features may be removed and/or added from/to any embodiment.

In one aspect, a data management system may generate a variety of reports, including 3 and/or 5 and/or 7 day reports of AS data and/or BG data. In certain embodiments, all or substantially all data processing is performed by the DMS, e.g., calibration of AS data, data analysis, mining, aggregation, filtering, and other suitable or desirable data processing functions including for example, therapy based analysis.

Data may be encrypted/decrypted and/or password protected for communication or transfer over one or more data networks or using one or more data communication protocol described above, for example. Additionally, data integrity and validation may be performed, for example, for detecting and/or correcting errors in the transmitted data using, for example, but not limited to, cyclic redundancy code (CRC), Manchester encoding/decoding, and the like. The AS system may include a unique identifier which may be known at the remote site (e.g., by the HCP system), to ensure data is correctly attributed to the correct user at the HCP site. Embodiments include various patient privacy protections, e.g., in accordance with The Health Insurance Portability and Accountability Act (HIPAA). In other words, systems herein may be HIPAA compliant.

In certain embodiments, data may be directly, e.g., automatically, transferred into a user's medical records (electronic record), billing data, etc. e.g., from the DMS. Embodiments include those capable to complete seamless downloads to electronic medical records systems. In certain embodiments, a reimbursement code may be automatically determined by the system for the HCP, e.g., Medical and/or Medicaid and/or various state codes. Determining such codes may be time consuming and complex. An analyte system that performs this task would be a great benefit to HCPs and users. For example, a reimbursement code may be determined by a system such as a DMS and displayed audibly and/or visually on a user interface display. The code may be automatically entered into a patient's records and/or reimbursement files and "paperwork". Embodiments include those capable to complete seamless identification of reimbursement code(s) and/or download such to one or more compatible electronic systems. Accordingly, certain embodiments are self-documenting.

As noted above, embodiments are configured to ensure patient privacy, e.g., are HIPAA compliant. For example, as described above some embodiments include components that may be used by more than one individual. Patient data may be patient identification (ID) identified and all patient data from a first user may be automatically deleted from the system or one or more system components when the system is configured for a second user, e.g., by an HCP. For example, an AS data processing unit and/or receiving unit may require an initialization procedure for each use or user, e.g., performed by an HCP or the user, which requires entry of a password or other unique patient identifier. Patient specific data may be automatically deleted or the initializer may be prompted to delete during initialization of the CG system. Likewise, patient specific data may be scrambled, encrypted, or otherwise rendered indiscernible. Patient data may be deleted based on a time schedule in certain embodiments.

The AS systems and methods may be applicable for Type I and Type II diabetics, newly diagnosed diabetics, patients experiencing diabetic condition, post surgery glycemic control and the like. The AS systems and methods may be used in conjunction with multiple users or patients, for data analysis or therapy management.

The components of the embodiments herein may be combined in a single housing or may be separate. Further, embodiments may be re-usable, such that, they may be used by a plurality of users. In certain embodiments, DMS may be a PC based application, e.g., a Windows application.

Embodiments may include a module that (1) supports bidirectional or unidirectional RF (or infrared "IR", or Bluetooth®) communication between the module and a CG transmitter unit and/or Data Logger, and/or (2) communicates to a BG meter via a wired connection (such as a cable or set of contacts), (3) communicates to a data processing terminal such as a PC (e.g., unit 105) via RF, IR or a wired cable, and/or contains a microprocessor (CPU) to handle all of the communication and data processing tasks.

For example, a module may serve as a communications hub between a BG meter, a PC and a CG transmitter or Data Logger, thereby enabling CG-BG calibration, the display of CG data on the BG meter, data transfer to a DMS, and data collection for retrospective or prospective analysis. By having this capability, the overall system is very cost effective and easy to use since the display and BG capabilities of the BG meter aren't duplicated elsewhere in the system, and the overall system would have complete CG functionality without adding any significant extra cost to the base HCP meter.

Accordingly, an analyte monitoring device such as an assessor in one embodiment may include a data collection module for receiving and storing analyte data over a predetermined time period from a subject, a user interface unit coupled to the data collection module for providing one or more indication related to the analyte data, a control unit coupled to the data collection module and the user interface unit to control, at least in part the operation of the data collection module and the user interface unit, and a communication module coupled to the control unit for communicating one or more signals associated with the analyte data to a remote location, where the user interface unit is configured to operate in a prospective analysis mode including substantially real time output of the analyte level received by the data collection module, and a retrospective analysis mode including limited output of information to the subject during the predetermined time period, and further where the communication module is configured to communicate with the remote location after the analyte data is received and stored in the data collection module over the predetermined time period.

The device may include a strip port operatively coupled to the control unit for receiving a blood glucose test strip.

The communication module in one embodiment may be configured to communicate with the remote location using one or more of a USB cable connection, a serial cable connection, an RF communication protocol, an infrared communication protocol, a Bluetooth® communication protocol, or an 802.11x communication protocol.

The user interface unit may be configured to not display any information related to the received analyte data in the retrospective analyte mode.

In one aspect, the limited output of information during the retrospective analysis mode may include output to the user interface unit of one or more of the analyte monitoring device operational status information, a time of day information, a user profile information, or the elapsed duration of the predetermined time period.

The data collection module may include one or more of a data storage device or a memory device, where the memory device may be a random access memory.

In another aspect, the data collection module may be configured to delete the stored analyte data after transferring the analyte data to the remote location.

The remote location may include a data processing terminal such as an HCP PC terminal.

In a further aspect, during the prospective analysis mode, the user interface unit may be configured to visually output real time information related to the received analyte data of the subject, where the visual output may include one or more of a graphical output, a numerical output, or a text output.

The stored analyte data in the data collection module may be uncalibrated.

The communicated one or more signals associated with the analyte data to the remote location may include uncalibrated analyte data.

In a further aspect, the communication module may be configured to receive one or more calibration information, where the calibration information may include blood glucose data.

Also, the control unit may be configured to calibrate the received and stored analyte data based on the received calibration information to generate calibrated analyte data, where the data collection module may be configured to store the calibrated analyte data.

Further, the communication module may be configured to transmit the calibrated analyte data to the remote location.

A method in another embodiment may include storing analyte data over a predetermined time period received from a subject, providing one or more indication related to the received analyte data on a user interface unit, including operating the user interface unit in a prospective analysis mode including substantially real time output of the analyte level received by the data collection module, and a retrospective analysis mode including limited output of information to the subject during the predetermined time period, and communicating one or more signals associated with the analyte data to a remote location after the analyte data is received and stored over the predetermined time period.

The method in another aspect may include receiving a blood glucose test data.

The method may also include communicating with the remote location using one or more of a USB cable connection, a serial cable connection, an RF communication protocol, an infrared communication protocol, a Bluetooth® communication protocol, or an 802.11x communication protocol.

The method may include not displaying any information related to the received analyte data in the retrospective analyte mode.

The limited output of information during the retrospective analysis mode may include outputting one or more of an operational status information, a time of day information, a user profile information, or the elapsed duration of the predetermined time period.

In still another aspect, the method may include deleting the stored analyte data after transferring the analyte data to the remote location.

Also, during the prospective analysis mode, the method may include visually outputting real time information related to the received analyte data of the subject, where the visual output may include one or more of a graphical output, a numerical output, or a text output.

In another aspect, the stored analyte data may be uncalibrated.

The method may include transmitting uncalibrated analyte data to the remote location.

Further, the method in yet another aspect may include receiving one or more calibration information, where the calibration information may include blood glucose data.

In yet a further aspect, the method may include calibrating the received and stored analyte data based on the received calibration information to generate calibrated analyte data.

The method may also include storing the calibrated analyte data.

Additionally, the method may include transmitting the calibrated analyte data to the remote location.

In yet a further aspect, the in vitro blood glucose meter may be configured to output or otherwise display the analyte sensor data, where the blood glucose meter includes a memory unit such as random access memory or other similar storage unit to store the analyte sensor data (which may be a one minute analyte related data over a time period of one to seven days, for example). Other time periods for the storage of analyte related data may be contemplated including, for example, longer than seven days, and further, the each analyte related data may be a five minute data or 10 minute data, for example.

In another aspect, the clocks in the in vitro blood glucose meter and the receiver unit (FIG. 1) may be time synchronized initially or during use, or periodically, such that the blood glucose value obtained by the in vitro blood glucose meter has a time corresponding analyte sensor data from the analyte sensor 101 (FIG. 1).

Various other modifications and alterations in the structure and method of operation of the present disclosure will be apparent to those skilled in the art without departing from the scope and spirit of the present disclosure. Although the present disclosure has been described in connection with specific embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:

1. A healthcare provider receiving device for glucose data obtained from a plurality of patients of a healthcare provider, comprising:
    a wireless communication component configured to communicate with each of a plurality of glucose monitoring systems, each of the plurality of glucose monitoring systems comprising one or more data processing units coupled to a corresponding transcutaneous glucose sensor, each corresponding transcutaneous glucose sensor configured to be positioned at least in part in contact with a fluid under a skin layer of a patient of the plurality of patients of the healthcare provider, each one or more data processing units configured to generate glucose data of a corresponding patient of the plurality of patients from the corresponding transcutaneous glucose sensor, each one or more data processing units having a memory configured to store corresponding glucose data generated during an entire wear period of several days to weeks;
    a USB port; and
    one or more processors configured to, for each patient:
        cause an operational status of the corresponding glucose monitoring system to be displayed at the healthcare provider receiving device during the wear period,
        obtain the stored glucose data of the patient from the corresponding one or more data processing units, wherein the receiver does not allow the patient to view the stored glucose data such that the patient is blinded during the entire wear period, and
        transmit the glucose data of the patient to a healthcare provider computing device using the USB port.

2. The device of claim 1, wherein the glucose data transmitted to the healthcare provider computing device comprises calibrated glucose data.

3. The device of claim 1, wherein the one or more processors are further configured to transmit a unique identifier to the healthcare provider computing device, wherein the unique identifier is used by a remote server associate the glucose data with the corresponding patient of the plurality of patients.

4. The device of claim 3, wherein the unique identifier comprises identification information of the one or more data processing units.

5. The device of claim 4, wherein the unique identifier is encrypted.

6. The device of claim 1, wherein the one or more processors are configured to check for errors in the transmitted glucose data using cyclic redundancy checks.

7. The device of claim 1, wherein the operational status comprises an indication of system integrity.

8. The device of claim 1, wherein the operational status comprises a duration of data collection.

9. The device of claim 1, wherein the wireless communication component is configured to communicate with each of the plurality of glucose monitoring systems by a Bluetooth protocol.

10. A healthcare provider monitoring system for glucose data obtained from a plurality of patients of a healthcare provider, comprising:
    a plurality of glucose monitoring systems, each of the plurality of glucose monitoring systems comprising:
        a transcutaneous glucose sensor configured to be positioned at least in part in contact with a fluid under a skin layer of a patient of the plurality of patients of the healthcare provider, and
        one or more data processing units coupled to the transcutaneous glucose sensor and configured to generate glucose data from the transcutaneous glucose sensor, the one or more data processing units having a memory configured to store the glucose data generated during an entire wear period of several days to weeks, and
    a healthcare provider receiving device comprising:
        a wireless communication component configured to communicate with each of the plurality of glucose monitoring systems,
        a USB port, and
        one or more processors configured to, for each patient:
            cause an operational status of the corresponding glucose monitoring system to be displayed at the healthcare receiving device during the wear period,
            obtain the stored glucose data of the patient from the corresponding one or more data processing units, wherein the receiver does not allow the patient to view the stored glucose data such that the patient is blinded during the entire wear period, and transmit the glucose data of the patient to a healthcare provider computing device using the USB port.

11. The system of claim 10, wherein the stored glucose data comprises calibrated glucose data.

12. The system of claim 10, wherein the stored glucose data comprises uncalibrated glucose data, and the uncalibrated glucose data is transformed into calibrated glucose data using the one or more processors with no user intervention.

13. The system of claim 10, wherein the stored glucose data comprises uncalibrated glucose data, and the uncalibrated glucose data is transformed into calibrated glucose data using the one or more processors without using an in vitro glucose test strip.

14. The system of claim 10, wherein the glucose data transmitted to the healthcare provider computing device comprises calibrated glucose data.

15. The system of claim 10, further comprising a remote server configured to receive the glucose data from the healthcare provider computing device via a network connection.

16. The system of claim 15, wherein the remote server is configured to provide access to the glucose data or a report of the glucose data via a network connection.

17. The system of claim 15, wherein the remote server is further configured to receive a patient identifier to associate the glucose data with the corresponding patient.

18. The system of claim 17, wherein the patient identifier is encrypted.

19. The system of claim 15, wherein the one or more processors and/or the remote server are configured to check for errors in the transmitted glucose data using cyclic redundancy checks.

20. The system of claim 10, wherein the one or more data processing units comprise an application specific integrated circuit configured to implement one or more routines associated with the generation and/or storage and/or calibration and/or Bluetooth communication of the glucose data.

21. The system of claim 10, wherein the operational status comprises an indication of system integrity.

22. The system of claim 10, wherein the operational status comprises a duration of data collection.

23. The system of claim 10, wherein the one or more data processing units comprise a Bluetooth transmitter.

* * * * *